United States Patent
Corbin et al.

(10) Patent No.: US 11,634,721 B2
(45) Date of Patent: Apr. 25, 2023

(54) RECONSTRUCTION OF SITE SPECIFIC NUCLEASE BINDING SITES

(71) Applicant: CORTEVA AGRISCIENCE LLC, Indianapolis, IN (US)

(72) Inventors: David R. Corbin, Chesterfield, MO (US); Wei Chen, Carmel, IN (US); Stephen Novak, Westfield, IN (US); Ryan M. Lee, Brownsburg, IN (US); Sandeep Kumar, Carmel, IN (US); Andrew Asberry, Indianapolis, IN (US); Andrew F. Worden, Indianapolis, IN (US)

(73) Assignee: DOW AGROSCIENCES LLC

( * ) Notice: Subject to any disclaimer, the term of this patent is extended or adjusted under 35 U.S.C. 154(b) by 41 days.

(21) Appl. No.: 15/833,168

(22) Filed: Dec. 6, 2017

(65) Prior Publication Data

US 2018/0163218 A1 Jun. 14, 2018

Related U.S. Application Data

(60) Provisional application No. 62/433,845, filed on Dec. 14, 2016.

(51) Int. Cl.
  *C12N 15/82* (2006.01)
  *C12N 9/22* (2006.01)
  *C12N 15/90* (2006.01)

(52) U.S. Cl.
  CPC .......... *C12N 15/8213* (2013.01); *C12N 9/22* (2013.01); *C12N 15/8209* (2013.01); *C12N 15/8261* (2013.01); *C12N 15/8274* (2013.01); *C12N 15/8286* (2013.01); *C12N 15/90* (2013.01); *C12Y 301/21004* (2013.01); *Y02A 40/146* (2018.01)

(58) Field of Classification Search
  None
  See application file for complete search history.

(56) References Cited

U.S. PATENT DOCUMENTS

| | | |
|---|---|---|
| 6,750,379 B2 | 6/2004 | MeElroy et al. |
| 7,736,886 B2 | 6/2010 | Puchta et al. |
| 7,838,295 B2 | 11/2010 | Gilbertson |
| 7,919,679 B2 | 4/2011 | Gilbertson |
| 8,148,607 B2 | 4/2012 | D'Halluin |
| 8,247,232 B2 | 8/2012 | Gilbertson |
| 2011/0191877 A1 | 8/2011 | Russell et al. |
| 2011/0191899 A1* | 8/2011 | Ainley ............... C12N 15/8201 800/278 |
| 2014/0304853 A1 | 10/2014 | Ainley et al. |
| 2016/0145645 A1* | 5/2016 | Bahr ................... C12N 15/907 435/69.1 |
| 2018/0171361 A1* | 6/2018 | Church ............. C12N 15/1132 |

FOREIGN PATENT DOCUMENTS

| | | |
|---|---|---|
| WO | WO2011090804 A1 | 7/2011 |
| WO | WO2011091311 A2 | 7/2011 |
| WO | WO2013169802 A1 | 4/2013 |

OTHER PUBLICATIONS

Dudas et al. DNA double-strand break repair by homologous recombination Mutat. Res. Mar. 2004;566(2):131-67. (Year: 2004).*
Wyman et al. DNA double-strand break repair: all's well that ends well. Ann. Rev. Genet. 2006;40:363-83. (Year: 2006).*
Petolino. Genome editing in plants via designed zinc finger nucleases. In Vitro Cell. Dev. Biol. Plant. 2015;51(1):1-8. Epub Jan. 29, 2015. (Year: 2015).*
Byrne et al. Multi-kilobase homozygous targeted gene replacement in human induced pluripotent stem cells.Nucleic Acids Res. Feb. 18, 2015;43(3):e21. Epub Nov. 20, 2014. (Year: 2014).*
Betermier et al. Is non-homologous end-joining really an inherently error-prone process? PloS Genet. Jan. 2014;10(1):e1004086. Epub Jan. 16, 2014. (Year: 2014).*
Coy of International Search Report and Written Opinion for International Application No. PCT/US2017/064838, dated Apr. 27, 2018.
European Search Report dated Aug. 6, 2020 for PCTUS2017064838.
Mauricio S Antunes et al "Targeted DNA excision in Arabidopsis by a re-engineered homing endonuclease." BMC biotechnology 12.1 (2012): 1-12.
Petolino G et al. "Zinc finger nuclease-mediated transgene deletion." Plant molecular biology 73.6 (2010): 617-628.
Bloor A et al "An efficient method of selectable marker gene excision by Xer recombination for gene replacement in bacterial chromosomes." Applied and environmental microbiology 72.4 (2006): 2520-2525.
Srivastava V et al "Dual-targeting by CRISPR/Cas9 for precise excision of transgenes from rice genome." Plant Cell, Tissue and Organ Culture (PCTOC) 129.1 (2017): 153-160.
International Preliminary Report On Patentability dated Jun. 12, 2017 for PCTUS2017064838.
International Search Report dated Apr. 27, 2018 or PCTUS2017064838.
Written Opinion dated Dec. 6, 2017 or PCTUS2017064838.

* cited by examiner

*Primary Examiner* — Cynthia E Collins

(57) ABSTRACT

Disclosed herein are methods and compositions for the repair of site specific nuclease binding sites by targeted integration and/or targeted excision of one or more sequences into a cell.

15 Claims, 12 Drawing Sheets

Specification includes a Sequence Listing.

Fig. 6:

```
SEQ ID NO:17-B104[1]/pDAB105826.2.137.1::pDAB118231.1.21.1=2521   TGGATCGTTCTTTCATGTAAAGACTCCCGCCCATCTCTC   eZFN2
SEQ ID NO:17-B104[1]/pDAB105826.2.137.1::pDAB118231.1.21.1=2522   TGGATCGTTCTTTCATGTAAAGACTCCCGCCCATCTCTC
SEQ ID NO:17-B104[1]/pDAB105826.2.137.1::pDAB118232.1.2.1=2524    TGGATCGTTCTTTCATGTAAAGACTCCCGCCCATCTCTC
SEQ ID NO:17-B104[1]/pDAB105826.2.137.1::pDAB118232.1.2.1=2525    TGGATCGTTCTTTCATGTAAAGACTCCCGCCCATCTCTC
SEQ ID NO:17-B104[1]/pDAB105826.2.137.1::pDAB118233.1.11.1=2539   TGGATCGTTCTTTCATGTAAAGACTCCCGCCCATCTCTC
SEQ ID NO:17-B104[1]/pDAB105826.2.137.1::pDAB118233.1.11.1=2541   TGGATCGTTCTTTCATGTAAAGACTCCCGCCCATCTCTC
SEQ ID NO:17-pDAB118231, pDAB118232, and pDAB118233               TGGATCGTTCTTTCATGTAAAGACTCCCGCCCATCTCTC Binding Site
B104[1]/pDAB105826.2.137.1::pDAB118231.1.21.1=2521   (41)   TATGCCCGGGACAAGTGTACATGATAACCTCAG
B104[1]/pDAB105826.2.137.1::pDAB118231.1.21.1=2522   (41)   TATGCCCGGGACAAGTGTACATGATAACCTCAG
B104[1]/pDAB105826.2.137.1::pDAB118232.1.2.1=2524    (41)   TATGCCCGGGACAAGTGTACATGATAACCTCAG
B104[1]/pDAB105826.2.137.1::pDAB118232.1.2.1=2525    (41)   TATGCCCGGGACAAGTGTACATGATAACCTCAG
B104[1]/pDAB105826.2.137.1::pDAB118233.1.11.1=2539   (41)   TATGCCCGGGACAAGTGTACATGATAACCTCAG
B104[1]/pDAB105826.2.137.1::pDAB118233.1.11.1=2541   (41)   TATGCCCGGGACAAGTGTACATGATAACCTCAG
pDAB118231, pDAB118232, and pDAB118233               (41)   TATGCCCGGGACAAGTGTACATGATAACCTCAG
```

RECONSTRUCTION OF SITE SPECIFIC NUCLEASE BINDING SITES

CROSS REFERENCE TO RELATED APPLICATION

The present application claims priority to the benefit of U.S. Provisional Patent Application Ser. No. 62/433,845 filed Dec. 14, 2016 the disclosure of which is hereby incorporated by reference in its entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: one 14.0 KB ASCII (Text) file named "78591-US-NP-20171004-Sequence-Listing-ST25.txt" created on Nov. 2, 2017.

BACKGROUND

Biotechnology has emerged as an essential tool in efforts to meet the challenge of increasing global demand for food production. Conventional approaches to improving agricultural productivity, e.g. enhanced yield or engineered pest resistance, rely on either mutation breeding or introduction of novel genes into the genomes of crop species by transformation. Both processes are inherently nonspecific and relatively inefficient. For example, conventional plant transformation methods deliver exogenous DNA that integrates into the genome at random locations. Thus, in order to identify and isolate transgenic lines with desirable attributes, it is necessary to generate thousands of unique random-integration events and subsequently screen for the desired individuals. As a result, conventional plant trait engineering is a laborious, time-consuming, and unpredictable undertaking. Furthermore, the random nature of these integrations makes it difficult to predict whether pleiotropic effects due to unintended genome disruption have occurred. As a result, the generation, isolation and characterization of plant lines with engineered genes or traits has been an extremely labor and cost-intensive process with a low probability of success.

In mammalian cells, stable transgenesis and targeted gene insertion have many potential applications in both gene therapy and cell engineering. However, current strategies are often inefficient and non-specifically insert the transgene into genomic DNA. The inability to control the location of genome insertion can lead to highly variable levels of transgene expression throughout the population due to position effects within the genome. Additionally, current methods of stable transgenesis and amplification of transgenes often result in physical loss of the transgene, transgene silencing over time, insertional mutagenesis by the integration of a gene and autonomous promoter inside or adjacent to an endogenous gene, the creation of chromosomal abnormalities and expression of rearranged gene products (comprised of endogenous genes, the inserted transgene, or both), and/or the creation of vector-related toxicities or immunogenicity in vivo from vector-derived genes that are expressed permanently due to the need for long-term persistence of the vector to provide stable transgene expression.

Targeted gene modification overcomes the logistical challenges of conventional practices in biological systems, and as such has been a long-standing but elusive goal in both basic plant biology research of agricultural biotechnology and applications in pharmaceutical therapeutic applications. However, with the exception of "gene targeting" via positive or negative drug selection or the use of pre-engineered restriction sites, targeted genome modification in biologicals species has until recently proven very difficult. Terada et al. (2002) *Nat Biotechnol* 20(10):1030; Terada et al. (2007) *Plant Physiol* 144(2):846; D'Halluin et al. (2008) Plant Biotechnology J. 6(1):93.

The methods and compositions for targeted cleavage of genomic DNA have been previously described. Such targeted cleavage events can be used, for example, to induce targeted mutagenesis, induce targeted deletions of cellular DNA sequences, and facilitate targeted recombination at a predetermined chromosomal locus. See, for example, United States Patent Publications 20030232410; 20050208489; 20050026157; 20050064474; 20080182332; and 20060188987, and International Publication WO 2007/014275, the disclosures of which are incorporated by reference in their entireties for all purposes.

However, there remain needs for compositions and methods for targeted integration, including for targeted integration into organisms for establishing stable, heritable genetic modifications in the plant and its progeny, and for target integration into mammalian cells for gene therapy and cell line development purposes.

SUMMARY

The present disclosure provides methods and compositions for a method for producing a repaired site specific nuclease binding site. In aspects of this embodiment, the method includes providing a genome comprising a first copy of a site specific nuclease binding site, an intervening polynucleotide sequence, and a second copy of the site specific nuclease binding site, wherein the first copy of the site specific nuclease binding site and the second copy of the site specific nuclease binding site are identical. In another aspect of this embodiment, the method includes introducing a site specific nuclease designed to bind and cleave at the site specific nuclease binding site. In a further aspect of this embodiment, the method includes cleaving the first copy of the site specific nuclease binding site. In other aspects of this embodiment, the method includes cleaving the second copy of the site specific nuclease binding site. In additional aspects of this embodiment, the method includes recombining the first cleaved site specific nuclease binding site with the second cleaved site specific nuclease binding site. In further aspects of this embodiment, the method includes producing the repaired site specific nuclease binding site, wherein the repaired site specific nuclease binding site is identical to the first copy of the site specific nuclease binding site. In further aspects of this embodiment, the method includes targeting the repaired site specific nuclease binding site with the site specific nuclease. In some aspects of this embodiment, the method includes cleaving the repaired site specific nuclease binding site with the site specific nuclease. In additional aspects of this embodiment, the method includes introducing a donor polynucleotide sequence. In some aspects of this embodiment, the method includes integrating the donor polynucleotide sequence within the cleaved site specific nuclease binding site. In further aspects of this embodiment, the method includes producing a genome comprising the donor polynucleotide sequence stably integrated within the genome.

In further embodiments, the site specific nuclease can be a Zinc Finger nuclease, a CRISPR nuclease, a TALEN nuclease, or any combination thereof. In some aspects of this embodiment, the Zinc Finger nuclease comprise a FokI nuclease. In other aspects of this embodiment, the FokI nuclease comprises a high fidelity FokI nuclease. In other embodiments, the intervening polynucleotide sequence is completely removed from the genome. In a further aspect of this embodiment, the intervening polynucleotide sequence comprises a transgene. In some aspects of the embodiment, the transgene encodes a selectable marker. In other embodiments, the repaired site specific nuclease binding site is repaired via a NHEJ-mediated cellular process. In some embodiments, the the repaired site specific nuclease binding site is greater than 6 bp in length. In additional embodiments, the first copy of the site specific nuclease binding site is located within 3,000 bp to 4,000 bp of the second copy of the site specific nuclease binding site. In some embodiments, the repaired site specific nuclease does not comprise an INDEL. In further embodiments, the first copy of the site specific nuclease binding site, the intervening polynucleotide sequence, and the second copy of the site specific nuclease comprise either a native genomic sequence or a transgenic sequence within a genome of a eukaryotic organism. In other embodiments, the intervening polynucleotide sequence comprises a polynucleotide encoding a transgene or a gene expression cassette. In some embodiments, the site specific nuclease binding site is palindromic. In additional embodiments, the site specific nuclease binding site is non-palindromic. In further embodiments, the first site specific nuclease binding site is arranged in a direct repeat orientation with the second site specific nuclease binding site. In other embodiments, the first site specific nuclease binding site is arranged in a palindromic orientation with the second site specific nuclease binding site. In further embodiments, the repaired site specific nuclease binding site is inherited in a progeny.

The present disclosure provides methods and compositions for a plant comprising a repaired site specific nuclease binding site. In some embodiments, the plant comprises a transgenic event. In other embodiments, the transgenic event comprises an agronomic trait. In additional embodiments, the agronomic trait is selected from the group consisting of an insecticidal resistance trait, herbicide tolerance trait, nitrogen use efficiency trait, water use efficiency trait, nutritional quality trait, DNA binding trait, small RNA trait, selectable marker trait, or any combination thereof. In an aspect of the embodiment, the agronomic trait comprises a herbicide tolerant trait. For example, the herbicide tolerant trait comprises a aad-1 coding sequence. In other embodiments, the transgenic plant produces a commodity product. In some aspects of this embodiment, the commodity product is selected from the group consisting of protein concentrate, protein isolate, grain, meal, flour, oil, or fiber. In another embodiment, the transgenic plant is selected from the group consisting of a dicotyledonous plant or a monocotyledonous plant. In some aspects of this embodiment, the monocotyledonous plant is a *Zea mays* plant.

The present disclosure provides methods and compositions for a method for excising a transgene. Some aspects of this method includes cleaving a first copy of a site specific nuclease binding site. Other aspects of this method includes cleaving a second copy of a site specific nuclease binding site. Further aspects of this method includes recombining the first cleaved site specific nuclease binding site with the second cleaved site specific nuclease binding site. Additional aspects of this method includes producing a repaired site specific nuclease binding site, wherein the repaired site specific nuclease binding site is identical to the first copy of the site specific nuclease binding site. Some aspects of this method includes excising the transgene, wherein the transgene is located between the first copy of the site specific nuclease and the second copy of the site specific nuclease. Additional aspects of this method includes targeting the repaired site specific nuclease binding site with the site specific nuclease. Other aspects of this method includes cleaving the repaired site specific nuclease binding site with the site specific nuclease. Further aspects of this method includes introducing a donor polynucleotide sequence. Aspects of this method includes integrating the donor polynucleotide sequence within the cleaved site specific nuclease binding sites. Other aspects of this method includes producing a genome comprising the donor polynucleotide sequence stably integrated within the genome.

In further embodiments, the site specific nuclease can be a Zinc Finger nuclease, a CRISPR nuclease, a TALEN nuclease, or any combination thereof. In some aspects of this embodiment, the Zinc Finger nuclease comprise a FokI nuclease. In some embodiments, the donor polynucleotide sequence comprises a transgene.

The present disclosure provides methods and compositions for a method for the cellular repair of two nuclease cleavage sites. Further aspects of this method includes cleaving a first copy of a site specific nuclease binding site. Other aspects of this method includes cleaving a second copy of a site specific nuclease binding site. Some aspects of this method includes recombining the first cleaved site specific nuclease binding site with the second cleaved site specific nuclease binding site. Additional aspects of this method includes producing a repaired site specific nuclease binding site, wherein the repaired site specific nuclease binding site is identical to the first copy of the site specific nuclease binding site. Further aspects of this method includes excising a transgene located between the first copy of the site specific nuclease and the second copy of the site specific nuclease. Other aspects of this method includes targeting the repaired site specific nuclease binding site with the site specific nuclease. Some aspects of this method includes cleaving the repaired site specific nuclease binding site with the site specific nuclease. Additional aspects of this method includes introducing a donor polynucleotide sequence. Further aspects of this method includes integrating the donor polynucleotide sequence within the cleaved site specific nuclease binding site. Aspects of this method includes producing a genome comprising the donor polynucleotide sequence stably integrated within the genome.

In some embodiments, the site specific nuclease binding sites are cleaved by a Zinc Finger nuclease, a TALEN nuclease, or a CRISPR nuclease. In other embodiments, the donor polynucleotide sequence comprises a transgene. In further embodiments, the cellular repair occurs during a phase of the cell cycle. In additional embodiments, the the phase of the cell cycle is selected from the group consisting of the gap 2 (G2) cell cycle phase, the gap 1 ($G_1$) cell cycle phase, the DNA synthesis (S phase) cell cycle phase, the mitosis (M) cell cycle phase, and any combination thereof.

The present disclosure provides methods and compositions for a method for the crossing a first and second plant to excise a transgene. Further aspects of this method includes obtaining a first plant, wherein the genome of the first plant comprises a site specific nuclease. Additional aspects of this method includes obtaining a second plant, wherein the genome of the second plant comprises a first copy of a site specific nuclease binding site, the transgene, and a second copy of the site specific nuclease binding site. Some aspects of this method includes crossing the first and second plants. Other aspects of this method includes cleaving the first copy of the specific nuclease binding site.

Further aspects of this method includes cleaving the second copy of the site specific nuclease binding site. Aspects of this method includes recombining the first cleaved site specific nuclease binding site with the second cleaved site specific nuclease binding site. Some aspects of this method includes producing a repaired site specific nuclease binding site, wherein the repaired site specific nuclease binding site is identical to the first copy of the site specific nuclease binding site. Further aspects of this method includes excising the transgene located between the first copy of the site specific nuclease and the second copy of the site specific nuclease. Other aspects of this method include targeting the repaired site specific nuclease binding site with the site specific nuclease. Some aspects of this method includes cleaving the repaired site specific nuclease binding site with the site specific nuclease. Additional aspects of this method includes introducing a donor polynucleotide sequence. Further aspects of this method includes integrating the donor polynucleotide sequence within the cleaved site specific nuclease binding site. Aspects of this method includes producing a genome comprising the donor polynucleotide sequence stably integrated within the genome.

In some embodiments, the site specific nuclease binding sites are cleaved by a Zinc Finger nuclease, a TALEN nuclease, or a CRISPR nuclease. In other embodiments the method results in the production of a progeny plant that is produced, the progeny plant comprising the repaired site specific nuclease. In further embodiments, the donor polynucleotide sequence comprises a transgene.

The present disclosure provides methods and compositions for a method for producing a repaired site specific nuclease binding site. Further aspects of this method includes providing a genome comprising a first copy of a site specific nuclease binding site, an intervening polynucleotide sequence, and a second copy of the site specific nuclease binding site, wherein the first copy of the site specific nuclease binding site and the second copy of the site specific nuclease binding site are identical. Other aspects of this method includes introducing a site specific nuclease designed to bind and cleave at the site specific nuclease binding site. Some aspects of this method includes cleaving the first copy of the site specific nuclease binding site. Some aspects of this method includes cleaving the second copy of the site specific nuclease binding site. Further aspects of this method includes recombining the first cleaved site specific nuclease binding site with the second cleaved site specific nuclease binding site. Additional aspects of this method includes producing the repaired site specific nuclease binding site, wherein the repaired site specific nuclease binding site is capable of being bound and cleaved by the site specific nuclease.

The present disclosure provides methods and compositions for a chloroplast transit peptide sequence operably linked to a cry34Ab1 encoding polynucleotide. In some embodiments, the chloroplast transit peptide is a synthetic chloroplast transit peptide. In other embodiments, the chloroplast transit peptide is a TRAP 4 chloroplast transit peptide. In further embodiments, the chloroplast transit peptide is a TRAP 8 chloroplast transit peptide. In additional embodiments, the chloroplast transit peptide is a TRAP 12 chloroplast transit peptide. In an embodiment, the chloroplast transit peptide sequence operably linked to a cry34Ab1 encoding polynucleotide consists of SEQ ID NO:19. In another embodiment, the chloroplast transit peptide sequence operably linked to a cry34Ab1 encoding polynucleotide consists of SEQ ID NO:20. In a further embodiment, the chloroplast transit peptide sequence operably linked to a cry34Ab1 encoding polynucleotide consists of SEQ ID NO:21. In an embodiment, the chloroplast transit peptide sequence operably linked to a cry34Ab1 encoding polynucleotide comprises a polynucleotide with at least 85%, 87.5%, 90%, 91%, 92%, 93%, 94%, 95%, 96%, 97%, 98%, 99%, 99.5%, or 99.9% sequence identity with the polynucleotide sequence of SEQ ID NO:19 In an embodiment, the chloroplast transit peptide sequence operably linked to a cry34Ab1 encoding polynucleotide comprises a polynucleotide with at least 85%, 87.5%, 90%, 91%, 92%, 93%, 94%, 95%, 96%, 97%, 98%, 99%, 99.5%, or 99.9% sequence identity with the polynucleotide sequence of SEQ ID NO:20. In an embodiment, the chloroplast transit peptide sequence operably linked to a cry34Ab1 encoding polynucleotide comprises a polynucleotide with at least 85%, 87.5%, 90%, 91%, 92%, 93%, 94%, 95%, 96%, 97%, 98%, 99%, 99.5%, or 99.9% sequence identity with the polynucleotide sequence of SEQ ID NO:21.

BRIEF DESCRIPTION OF THE DRAWINGS

FIG. 6 is a sequence aligment showing the perfect repair of the site specific nuclease binding site in two transgenic events that were sequenced. Note that the sequence labeled as "pDAB118231, pDAB118232, and pDAB118233" is the expected sequence, and "B104[1]/pDAB105826.2.137.1::pDAB118231.1.21.1=2521" and "B104[1]/pDAB105826.2.137.1::pDAB118231.1.21.1=2522" and "B104[1]/pDAB105826.2.137.1::pDAB118232.1.2.1=2524" and "B104[1]/pDAB105826.2.137.1::pDAB118232.1.2.1=2525" and "B104[1]/pDAB105826.2.137.1::pDAB118233.1.11.1=2539" and "B104[1]/pDAB105826.2.137.1::pDAB118233.1.11.1=2541" are the sequenced events that correspond with Table 6. As shown in the alignment, the aad-1 gene expression cassette sequence flanked by the eZFN2 binding sites of pDAB8291, pDAB8292, and pDAB8293 have been excised at the eZFN2 binding sites and the repaired eZFN2 binding site sequence of the plant events shows no alterations or INDELS as compared to the original eZFN2 binding site sequence.

FIG. 10B. pDAB112797.

Figure 1:
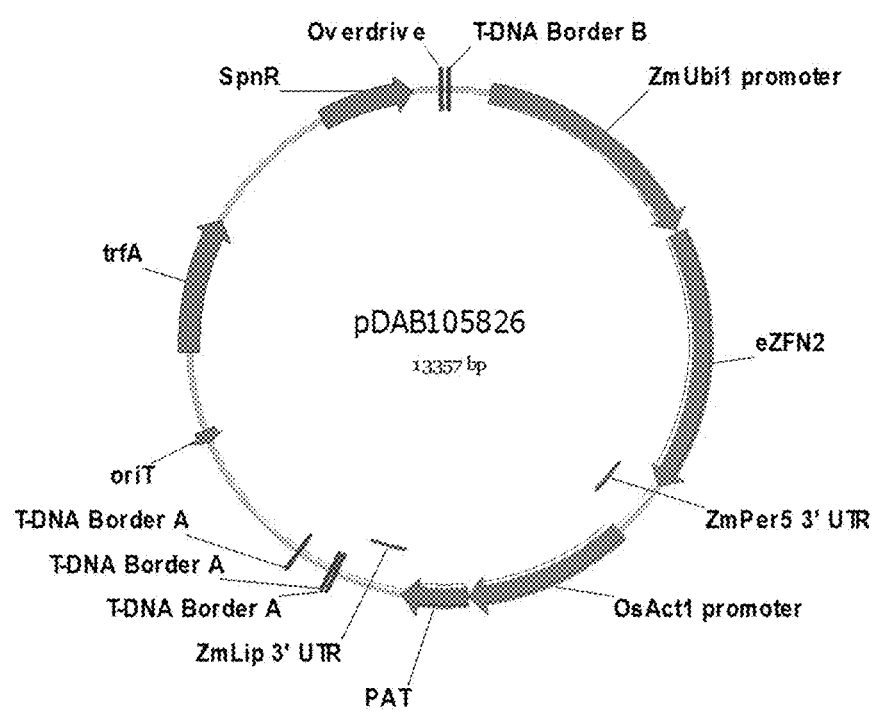
FIG. 1 is a schematic depicting a plasmid map of pDAB105826.

pDAB122423.3.84.1. The arrow indicates an event with complete excision of YFP as evidenced with no detectable qPCR signal. The oval indicates events with chimeric excision by a drop in detectable qPCR signal for YFP.

SEQUENCE LISTING

The nucleic acid sequences listed in the accompanying sequence listing are shown using standard letter abbreviations for nucleotide bases, as defined in 37 C.F.R. § 1.822. The nucleic acid and amino acid sequences listed define molecules (i.e., polynucleotides and polypeptides, respectively) having the nucleotide and amino acid monomers arranged in the manner described. The nucleic acid and amino acid sequences listed also each define a genus of polynucleotides or polypeptides that comprise the nucleotide and amino acid monomers arranged in the manner described. In view of the redundancy of the genetic code, it will be understood that a nucleotide sequence including a coding sequence also describes the genus of polynucleotides encoding the same polypeptide as a polynucleotide consisting of the reference sequence. It will further be understood that an amino acid sequence describes the genus of polynucleotide ORFs encoding that polypeptide.

Only one strand of each nucleic acid sequence is shown, but the complementary strand is understood as included by any reference to the displayed strand. As the complement and reverse complement of a primary nucleic acid sequence are necessarily disclosed by the primary sequence, the complementary sequence and reverse complementary sequence of a nucleic acid sequence are included by any reference to the nucleic acid sequence, unless it is explicitly stated to be otherwise (or it is clear to be otherwise from the context in which the sequence appears). Furthermore, as it is understood in the art that the nucleotide sequence of a RNA strand is determined by the sequence of the DNA from which it was transcribed (but for the substitution of uracil (U) nucleobases for thymine (T)), a RNA sequence is included by any reference to the DNA sequence encoding it.

DETAILED DESCRIPTION

The present disclosure relates to methods and compositions for producing site specific nuclease binding sites within a genome, for example a genome from a plant, a bacteria or a mammalian cell. An insertion polynucleotide target containing target sites for one or more nucleases (e.g., ZFNs) is integrated into the genome. Typically, the site specific nuclease binding sites flank a polynucleotide sequence. Following integration of the insertion polynucleotide target into the genome, the appropriate nucleases are introduced into the cell. In some examples, an exogenous sequence is also introduced into the cell for insertion within the genome of the cell.

In certain embodiments, the site specific nuclease(s) comprise one or more ZFNs, CRISPRS, or TALENS. The resulting cleavage of the recognition domain by the site specific nuclease usually results in the modification of the recognition domain to contain insertions and deletions (e.g., INDELS) that result in the alteration of the recognition domain to the extent that the site specific nuclease binding site can no longer be re-cleaved by the site specific nuclease used to initially make the double strand break. This requires the development of new site specific nucleases for subsequent rounds of cleavage of the modified recognition domain; a time consuming and monetary expensive endeavor. The development of methods that result in the perfect repair of a recognition domain that is cleaved by a site specific nuclease provide significant benefits. For example, recombining the binding site of a recognition sequence allows for the same site specific nuclease to be redeployed to bind and cleave the recognition sequence. More importantly, it enables a systematic approach to transgenic design, such that the same unique target site can be used and reused to either excise the gene out or to target additional genes for stacking within close proximity of the recognition sequence. Additionally, this method can simplify strategies of stacking into a single locus that is driven by site specific nuclease-dependent double-strand breaks.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, Second edition-1989 and Third edition-2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Was sarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

Throughout the application, a number of terms are used. In order to provide a clear and consistent understanding of the specification and claims, including the scope to be given such terms, the following definitions are provided.

As used herein, the articles, "a," "an," and "the" include plural references unless the context clearly and unambiguously dictates otherwise.

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970 WO 01/88197 and WO 02/099084.

A "zinc finger nuclease(s)" (ZFN or ZFNs) are zinc finger proteins that typically comprise a cleavage domain (or a cleavage half-domain) and a zinc finger binding domain. The ZFN may be introduced as proteins, as polynucleotides encoding these proteins or as combinations of polypeptides and polypeptide-encoding polynucleotides. Zinc finger nucleases typically function as dimeric proteins following dimerization of the cleavage half-domains. Obligate heterodimeric ZFNs, in which the ZFN monomers bind to the "left" and "right" recognition domains can associate to form an active nuclease have been described. See, e.g., U.S. Patent Publication No. 2008/0131962. A zinc finger binding domain can be a canonical (C2H2) zinc finger or a non-canonical (e.g., C3H) zinc finger. Furthermore, the zinc finger binding domain can comprise one or more zinc fingers (e.g., 2, 3, 4, 5, 6, 7, 8, 9 or more zinc fingers), and can be engineered to bind to any sequence within the insertion site. The presence of such a fusion protein (or proteins) in a cell will result in binding of the fusion protein(s) to its (their) binding site(s) and cleavage within the insertion site, which results in integration of the exogenous sequence(s).

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, ADVANCES IN APPLIED MATHEMATICS 2:482-489 (1981). This algorithm can be applied to amino acid sequences by using the scoring matrix developed by Dayhoff, ATLAS OF PROTEIN SEQUENCES AND STRUCTURE, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. Suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the internet. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; NUCLEIC ACID HYBRIDIZATION: A PRACTICAL APPROACH, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, NUCLEIC ACID HYBRIDIZATION: A PRACTICAL APPROACH, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., MOLECULAR CLONING: A LABORATORY MANUAL, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Recombining" refers to the combination of two binding sites to form a single binding site. In some examples, the two binding sites undergo recombination to form the single binding site.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage domain" comprises one or more polypeptide sequences which possesses catalytic activity for DNA cleavage. A cleavage domain can be contained in a single polypeptide chain or cleavage activity can result from the association of two (or more) polypeptides.

A "cleavage half-domain" is a polypeptide sequence which, in conjunction with a second polypeptide (either identical or different) forms a complex having cleavage activity (preferably double-strand cleavage activity).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a coding sequence for any polypeptide or fragment thereof, a functioning version of a malfunctioning endogenous molecule or a malfunctioning version of a normally-functioning endogenous molecule. Additionally, an exogenous molecule can comprise a coding sequence from another species that is an ortholog of an endogenous gene in the host cell.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression.

"Plant" cells include, but are not limited to, cells of monocotyledonous (monocots) or dicotyledonous (dicots) plants. Non-limiting examples of monocots include cereal plants such as maize, rice, barley, oats, wheat, sorghum, rye, sugarcane, pineapple, onion, banana, and coconut. Non-limiting examples of dicots include tobacco, tomato, sunflower, cotton, sugarbeet, potato, lettuce, melon, soybean, canola (rapeseed), and alfalfa. Plant cells may be from any part of the plant and/or from any stage of plant development.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

Binding Site

Disclosed in some embodiments herein is a method for repairing a polynucleotide sequence that is targeted by a site specific nuclease so that the resulting repaired polynucleotide sequence is identical to the first copy of the polynucleotide sequence. The resulting polynucleotide sequence can be re-targeted by the site specific nuclease in subsequent experiments. Such a method provides advantages for those skilled in the art, for instance the design and development of new site specific nucleases are not required to be produced, thereby reducing costs and time associated with the development of a new site specific nuclease for cleavage of the polynucleotide sequence. In addition, the introduction of additional insertion binding sites within a construct are not required as only a single polynucleotide binding site is necessary for targeting of a donor or excision of genes or other regulatory elements.

Further disclosed in some embodiments herein is a method for repairing a polynucleotide sequence that is targeted by a site specific nuclease so that the resulting repaired polynucleotide sequence is capable of being recognized, bound and cleaved by the site specific nuclease. The resulting polynucleotide sequence can be re-targeted by the site specific nuclease in subsequent experiments. Such a method provides advantages for those skilled in the art, for instance the design and development of new site specific nucleases are not required to be produced, thereby reducing costs and time associated with the development of a new site specific nuclease for cleavage of the polynucleotide sequence. In addition, the introduction of additional insertion binding sites within a construct are not required as only a single polynucleotide binding site is necessary for targeting of a donor or excision of genes or other regulatory elements.

The polynucleotide sequence that is targeted by a site specific nuclease may be described as a unique binding site, as a site specific binding site, as a target site, as a target sequence, as a binding site or as an insertion site. Namely, the polynucleotide sequence comprises a plurality of zinc finger nuclease (ZFN) binding sites such that, upon binding of the appropriate ZFN pair, the binding site is cleaved between the target sites of the ZFN pair. However, in other aspects the polynucleotide sequence comprises a TALEN binding sequence such that, upon binding of the appropriate TALEN nuclease, the site is cleaved between the target sites of the TALEN nuclease. In further aspects the polynucleotide sequence comprises a CRISPR binding sequence such that, upon binding of the appropriate CRISPR nuclease, the site is cleaved between the target sites of the CRISPR nuclease. Generally, the polynucleotide sequence comprises a site specific nuclease binding sequence such that, upon binding of the appropriate site specific nuclease enzyme, the site is cleaved between the target sites of the site specific nuclease enzymes.

The target site includes polynucleotides sequences not found in the genome of the cell into which it is integrated. As such, the occurrence of unwanted cleavage within the genome is reduced or eliminated. For zinc finger nucleases the target sites are typically in pairs such that the zinc finger nucleases form homo- or hetero-dimers to cleave at the appropriate site.

The insertion site may include targets sites bound by only homodimers, target sites bound by only heterodimers, or a combination of target sites bound by homo- and heterodimers. Target sites bound by homodimers may be utilized in some cases for one or more of the following reasons: delivery of one ZFN may be more efficient than two, homodimerization reduces the issue of unequal stoichiometry due to unequal expression of ZFNs; toxicity from cleavage at off-target sites may be reduced; the homodimer is half as likely to be disrupted by when using CCHC (non-canonical) zinc finger domains; and/or the total number of unique targetable sites can be expanded.

It will be apparent that it is not necessary for a target site to be a multiple of three nucleotides for zinc finger nucleases. For example, in cases in which cross-strand interactions occur (see, e.g., U.S. Pat. No. 6,453,242 and WO 02/077227), one or more of the individual zinc fingers of a multi-finger binding domain can bind to overlapping quadruplet subsites. As a result, a three-finger protein can bind a 10-nucleotide sequence, wherein the tenth nucleotide is part of a quadruplet bound by a terminal finger, a four-finger protein can bind a 13-nucleotide sequence, wherein the thirteenth nucleotide is part of a quadruplet bound by a terminal finger, etc.

The length and nature of amino acid linker sequences between individual zinc fingers in a multi-finger binding domain also affects binding to a target sequence. For example, the presence of a so-called "non-canonical linker," "long linker" or "structured linker" between adjacent zinc fingers in a multi-finger binding domain can allow those fingers to bind subsites which are not immediately adjacent. Non-limiting examples of such linkers are described, for example, in U.S. Pat. No. 6,479,626 and WO 01/53480. Accordingly, one or more subsites, in a target site for a zinc finger binding domain, can be separated from each other by 1, 2, 3, 4, 5 or more nucleotides. To provide but one example, a four-finger binding domain can bind to a 13-nucleotide target site comprising, in sequence, two contiguous 3-nucleotide subsites, an intervening nucleotide, and two contiguous triplet subsites.

Distance between sequences (e.g., target sites) refers to the number of nucleotides or nucleotide pairs intervening between two sequences, as measured from the edges of the sequences nearest each other.

In certain embodiments in which cleavage depends on the binding of two zinc finger domain/cleavage half-domain fusion molecules to separate target sites, the two target sites can be on opposite DNA strands. In other embodiments, both target sites are on the same DNA strand.

In other embodiments the target sites that flank the intervening polynucleotide sequence are arranged as direct repeats. In some aspects of this embodiment, both target sites are located on the sense strand. In some aspects of this embodiment, one target site is located on the sense strand and the second target site is located on the antisense strand. In other aspects of this embodiment, one target site is located upstream of the intervening polynucleotide sequence and is provided in multiple copies of 2, 3, 4, 5, 6 or more target sites. In further aspects of this embodiment, one target site is located downstream of the intervening polynucleotide sequence and is provided in multiple copies of 2, 3, 4, 5, 6 or more target sites.

In additional embodiments the target sites that flank the intervening polynucleotide sequence are arranged as as palindromic sequences. In some aspects of this embodiment, both target sites are located on the sense strand. In some aspects of this embodiment, one target site is located on the sense strand and the second target site is located on the antisense strand. In other aspects of this embodiment, one target site is located upstream of the intervening polynucleotide sequence and is provided in multiple copies of 2, 3, 4, 5, 6 or more target sites. In further aspects of this embodiment, one target site is located downstream of the intervening polynucleotide sequence and is provided in multiple copies of 2, 3, 4, 5, 6 or more target sites.

The insertion site can be integrated anywhere in the plant genome within an endogenous genomic DNA sequence. In certain embodiments, the insertion site is integrated into a Zp15 gene in the maize genome, which as described in U.S. application Ser. No. 12/653,735 is a desirable site for targeted integration of exogenous sequences. In other embodiments the insertion site is integrated into a maize preferred loci, which as described in U.S. application Ser. No. 14/531,739 is a desirable site for targeted integration of exogenous sequences. In further embodiments the insertion site is integrated into a soybean preferred loci, which as described in U.S. application Ser. No. 14/531,732 is a desirable site for targeted integration of exogenous sequences.

DNA-Binding Domains

Any DNA-binding domain can be used in the methods disclosed herein. In certain embodiments, the DNA binding domain comprises a zinc finger protein. A zinc finger binding domain comprises one or more zinc fingers. Miller et al. (1985) *EMBO J.* 4:1609-1614; Rhodes (1993) *Scientific American* February:56-65; U.S. Pat. No. 6,453,242. The zinc finger binding domains described herein generally include 2, 3, 4, 5, 6 or even more zinc fingers.

Typically, a single zinc finger domain is about 30 amino acids in length. Structural studies have demonstrated that each zinc finger domain (motif) contains two beta sheets (held in a beta turn which contains the two invariant cysteine residues) and an alpha helix (containing the two invariant histidine residues), which are held in a particular conformation through coordination of a zinc atom by the two cysteines and the two histidines.

Zinc fingers include both canonical $C_2H_2$ zinc fingers (i.e., those in which the zinc ion is coordinated by two cysteine and two histidine residues) and non-canonical zinc fingers such as, for example, $C_3H$ zinc fingers (those in which the zinc ion is coordinated by three cysteine residues and one histidine residue) and $C_4$ zinc fingers (those in which the zinc ion is coordinated by four cysteine residues). See also WO 02/057293 and also U.S. Patent Publication No. 20080182332 regarding non-canonical ZFPs for use in plants.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Enhancement of binding specificity for zinc finger binding domains has been described, for example, in co-owned WO 02/077227.

Since an individual zinc finger binds to a three-nucleotide (i.e., triplet) sequence (or a four-nucleotide sequence which can overlap, by one nucleotide, with the four-nucleotide binding site of an adjacent zinc finger), the length of a sequence to which a zinc finger binding domain is engineered to bind (e.g., a target sequence) will determine the number of zinc fingers in an engineered zinc finger binding domain. For example, for ZFPs in which the finger motifs do not bind to overlapping subsites, a six-nucleotide target sequence is bound by a two-finger binding domain; a nine-nucleotide target sequence is bound by a three-finger binding domain, etc. As noted herein, binding sites for individual zinc fingers (i.e., subsites) in a target site need not be contiguous, but can be separated by one or several nucleotides, depending on the length and nature of the amino acids sequences between the zinc fingers (i.e., the inter-finger linkers) in a multi-finger binding domain.

In a multi-finger zinc finger binding domain, adjacent zinc fingers can be separated by amino acid linker sequences of approximately 5 amino acids (so-called "canonical" inter-finger linkers) or, alternatively, by one or more non-canonical linkers. See, e.g., co-owned U.S. Pat. Nos. 6,453,242 and 6,534,261. For engineered zinc finger binding domains comprising more than three fingers, insertion of longer ("non-canonical") inter-finger linkers between certain of the zinc fingers may be desirable in some instances as it may increase the affinity and/or specificity of binding by the binding domain. See, for example, U.S. Pat. No. 6,479,626 and WO 01/53480. Accordingly, multi-finger zinc finger binding domains can also be characterized with respect to the presence and location of non-canonical inter-finger linkers. For example, a six-finger zinc finger binding domain comprising three fingers (joined by two canonical inter-finger linkers), a long linker and three additional fingers (joined by two canonical inter-finger linkers) is denoted a 2×3 configuration. Similarly, a binding domain comprising two fingers (with a canonical linker therebetween), a long linker and two additional fingers (joined by a canonical linker) is denoted a 2×2 configuration. A protein comprising three two-finger units (in each of which the two fingers are joined by a canonical linker), and in which each two-finger unit is joined to the adjacent two finger unit by a long linker, is referred to as a 3×2 configuration.

The presence of a long or non-canonical inter-finger linker between two adjacent zinc fingers in a multi-finger binding domain often allows the two fingers to bind to subsites which are not immediately contiguous in the target sequence.

Accordingly, there can be gaps of one or more nucleotides between subsites in a target site; i.e., a target site can contain one or more nucleotides that are not contacted by a zinc finger. For example, a 2×2 zinc finger binding domain can bind to two six-nucleotide sequences separated by one nucleotide, i.e., it binds to a 13-nucleotide target site. See also Moore et al. (2001a) Proc. Natl. Acad. Sci. USA 98:1432-1436; Moore et al. (2001b) Proc. Natl. Acad. Sci. USA 98:1437-1441 and WO 01/53480.

As mentioned previously, a target subsite is a three- or four-nucleotide sequence that is bound by a single zinc finger. For certain purposes, a two-finger unit is denoted a "binding module." A binding module can be obtained by, for example, selecting for two adjacent fingers in the context of a multi-finger protein (generally three fingers) which bind a particular six-nucleotide target sequence. Alternatively, modules can be constructed by assembly of individual zinc fingers. See also WO 98/53057 and WO 01/53480.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128.

As another alternative, the DNA-binding domain may be derived from a leucine zipper protein. Leucine zippers are a class of proteins that are involved in protein-protein interactions in many eukaryotic regulatory proteins that are important transcriptional factors associated with gene expression. The leucine zipper refers to a common structural motif shared in these transcriptional factors across several kingdoms including animals, plants, yeasts, etc. The leucine zipper is formed by two polypeptides (homodimer or heterodimer) that bind to specific DNA sequences in a manner where the leucine residues are evenly spaced through an α-helix, such that the leucine residues of the two polypeptides end up on the same face of the helix. The DNA binding specificity of leucine zippers can be utilized in the DNA-binding domains disclosed herein.

In some embodiments, the DNA-binding domain of one or more of the nucleases comprises a naturally occurring or engineered (non-naturally occurring) TAL effector DNA binding domain or a TALEN. See, e.g., U.S. Patent Publication No. 20110301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than different effector proteins into the plant cell.

Among these injected proteins are transcription activator-like (TALEN) effectors which mimic plant transcriptional activators and manipulate the plant transcriptome (see Kay et al., (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al., (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al., (2006) *J Plant Physiol* 163(3): 256-272). In addition, in the phytopathogenic bacteria *Ralstonia solanacearum* two genes, designated brg11 and hpx17 have been found that are homologous to the AvrB s3 family of *Xanthomonas* in the *R. solanacearum* biovar strain GMI1000 and in the biovar 4 strain RS1000 (See Heuer et al., (2007) *Appl and Enviro Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of Xanthomonas. See, e.g., U.S. Patent Publication No. 20110301073, incorporated by reference in its entirety.

Specificity of these TAL effectors depends on the sequences found in the tandem repeats. The repeated sequence comprises approximately 102 bp and the repeats are typically 91-100% homologous with each other (Bonas et al., ibid). Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence (see Moscou and Bogdanove, (2009) *Science* 326:1501 and Boch et al., (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al., ibid). Engineered TAL proteins have been linked to a FokI cleavage half domain to yield a TAL effector domain nuclease fusion (TALEN) exhibiting activity in a yeast reporter assay (plasmid based target).

The CRISPR (Clustered Regularly Interspaced Short Palindromic Repeats)/Cas (CRISPR Associated) nuclease system is a recently engineered nuclease system based on a bacterial system that can be used for genome engineering. It is based on part of the adaptive immune response of many bacteria and Archaea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA called a "protospacer". Cas9 cleaves the DNA to generate blunt ends at the DSB at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence (see Jinek et al (2012) Science 337, p. 816-821, Jinek et al, (2013), eLife 2:e00471, and David Segal, (2013) eLife 2:e00563). In other examples, the crRNA associates with the tracrRNA to guide the Cpf1 nuclease to a region homologous to the crRNA to cleave DNA with staggered ends (see Zetsche, Bernd, et al. *Cell* 1613 (2015): 759-771). Thus, the CRISPR/Cas system can be engineered to create a double-stranded break (DSB) at a desired target in a genome, and repair of the DSB can be influenced by the use of repair inhibitors to cause an increase in error prone repair.

In certain embodiments, the site specific nuclease protein may be a "functional derivative" of a naturally occurring site specific nuclease protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a site specific nuclease protein polypeptide or a fragment thereof include but are not limited to mutants, fusions, covalent modifications of site specific nuclease protein or a fragment thereof. Site specific nuclease protein, which includes zinc fingers, talens, CRISPR cas9, CRISPR cpf1 or a fragment thereof, as well as derivatives of site specific nuclease proteins or a fragment thereof, may be obtainable from a cell or synthesized chemically or by a combination of these two procedures. The cell may be a cell that naturally produces site specific nuclease protein, or a cell that naturally produces site specific nuclease protein and is genetically engineered to produce the endogenous site specific nuclease protein at a higher expression level or to produce a site specific nuclease protein from an exogenously introduced nucleic acid, which nucleic acid encodes a site specific nuclease protein that is same or different from the endogenous site specific nuclease protein. In some case, the cell does not naturally produce the site specific nuclease protein and is genetically engineered to produce a site specific nuclease protein. The site specific nuclease protein is deployed in plant cells by co-expressing the site specific nuclease protein with other domains that impart functionality to the site specific nuclease protein (e.g., guide RNA for CRISPR; wo forms of guide RNAs can be used to facilitate Cas-mediated genome cleavage as disclosed in Le Cong, F., et al., (2013) Science 339(6121): 819-823).

Cleavage Domains

As noted above, the DNA-binding domain may be associated with a cleavage (nuclease) domain. For example, homing endonucleases may be modified in their DNA-binding specificity while retaining nuclease function. In addition, zinc finger proteins may also be fused to a cleavage domain to form a zinc finger nuclease (ZFN). The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases, Cold Spring Harbor Laboratory Press,* 1993). Non limiting examples of homing endonucleases and meganucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. One or more of these enzymes (or functional fragments thereof) can be used as a source of cleavage domains and cleavage half-domains.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is FokI. This particular enzyme is active as a dimer. Bitinaite et al. (1998) *Proc. Natl. Acad. Sci. USA* 95: 10,570-10,575. Accordingly, for the purposes of the present disclosure, the portion of the FokI enzyme used in the disclosed fusion proteins is considered a cleavage half-domain. Thus, for targeted double-stranded cleavage and/or targeted replacement of cellular sequences using zinc finger-FokI fusions, two fusion proteins, each comprising a FokI cleavage half-domain, can be used to reconstitute a catalytically active cleavage domain. Alternatively, a single polypeptide molecule containing a zinc finger binding domain and two FokI cleavage half-domains can also be used. Parameters for targeted cleavage and targeted sequence alteration using zinc finger-FokI fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in co-owned International Publication WO 2007/014275, incorporated by reference herein in its entirety.

To enhance cleavage specificity, cleavage domains may also be modified. In certain embodiments, variants of the cleavage half-domain are employed these variants minimize or prevent homodimerization of the cleavage half-domains. Non-limiting examples of such modified cleavage half-domains are described in detail in WO 2007/014275, incorporated by reference in its entirety herein. See, also, Examples. In certain embodiments, the cleavage domain comprises an engineered cleavage half-domain (also referred to as dimerization domain mutants) that minimize or prevent homodimerization are known to those of skill the art and described for example in U.S. Patent Publication Nos. 20050064474 and 20060188987, incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains. See, e.g., U.S. Patent Publication Nos. 20050064474 and 20060188987; International Patent Publication WO 07/139898; Miller et al. (2007) *Nat. Biotechnol.* 25(7):778-785.

Additional engineered cleavage half-domains of FokI that form obligate heterodimers can also be used in the ZFNs described herein. In one embodiment, the first cleavage half-domain includes mutations at amino acid residues at positions 490 and 538 of FokI and the second cleavage half-domain includes mutations at amino acid residues 486 and 499.

In certain embodiments, the cleavage domain comprises two cleavage half-domains, both of which are part of a single polypeptide comprising a binding domain, a first cleavage half-domain and a second cleavage half-domain. The cleavage half-domains can have the same amino acid sequence or different amino acid sequences, so long as they function to cleave the DNA.

In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotides or more). In general, the point of cleavage lies between the target sites.

Fusion Proteins

Methods for design and construction of fusion proteins (and polynucleotides encoding same) are known to those of skill in the art. For example, methods for the design and construction of fusion proteins comprising DNA-binding domains (e.g., zinc finger domains) and regulatory or cleavage domains (or cleavage half-domains), and polynucleotides encoding such fusion proteins, are described in co-owned U.S. Pat. Nos. 6,453,242 and 6,534,261 and U.S. Patent Application Publications 2007/0134796 and 2005/0064474; herein incorporated by reference in their entireties. In certain embodiments, polynucleotides encoding the fusion proteins are constructed. These polynucleotides can be inserted into a vector and the vector can be introduced into a cell (see below for additional disclosure regarding vectors and methods for introducing polynucleotides into cells).

In certain embodiments of the methods described herein, a zinc finger nuclease comprises a fusion protein comprising a zinc finger binding domain and a cleavage half-domain from the FokI restriction enzyme, and two such fusion proteins are expressed in a cell. Expression of two fusion proteins in a cell can result from delivery of the two proteins to the cell; delivery of one protein and one nucleic acid encoding one of the proteins to the cell; delivery of two nucleic acids, each encoding one of the proteins, to the cell; or by delivery of a single nucleic acid, encoding both proteins, to the cell. In additional embodiments, a fusion protein comprises a single polypeptide chain comprising two cleavage half domains and a zinc finger binding domain. In this case, a single fusion protein is expressed in a cell and, without wishing to be bound by theory, is believed to cleave DNA as a result of formation of an intramolecular dimer of the cleavage half-domains.

In certain embodiments, the components of the fusion proteins (e.g., ZFP-FokI fusions) are arranged such that the zinc finger domain is nearest the amino terminus of the fusion protein, and the cleavage half-domain is nearest the carboxy-terminus. This mirrors the relative orientation of the cleavage domain in naturally-occurring dimerizing cleavage domains such as those derived from the FokI enzyme, in which the DNA-binding domain is nearest the amino terminus and the cleavage half-domain is nearest the carboxy terminus. In these embodiments, dimerization of the cleavage half-domains to form a functional nuclease is brought about by binding of the fusion proteins to sites on opposite DNA strands, with the 5' ends of the binding sites being proximal to each other.

In additional embodiments, the components of the fusion proteins (e.g., ZFP-FokI fusions) are arranged such that the cleavage half-domain is nearest the amino terminus of the fusion protein, and the zinc finger domain is nearest the carboxy-terminus. In these embodiments, dimerization of the cleavage half-domains to form a functional nuclease is brought about by binding of the fusion proteins to sites on opposite DNA strands, with the 3' ends of the binding sites being proximal to each other.

In yet additional embodiments, a first fusion protein contains the cleavage half-domain nearest the amino terminus of the fusion protein, and the zinc finger domain nearest the carboxy-terminus, and a second fusion protein is arranged such that the zinc finger domain is nearest the amino terminus of the fusion protein, and the cleavage half-domain is nearest the carboxy-terminus. In these embodiments, both fusion proteins bind to the same DNA strand, with the binding site of the first fusion protein containing the zinc finger domain nearest the carboxy terminus located to the 5' side of the binding site of the second fusion protein containing the zinc finger domain nearest the amino terminus.

In certain embodiments of the disclosed fusion proteins, the amino acid sequence between the zinc finger domain and the cleavage domain (or cleavage half-domain) is denoted the "ZC linker." The ZC linker is to be distinguished from the inter-finger linkers discussed above. See, e.g., U.S. Patent Publications 20050064474A1 and 20030232410, and International Patent Publication WO05/084190, for details on obtaining ZC linkers that optimize cleavage.

In one embodiment, the disclosure provides a ZFN comprising a zinc finger protein having one or more of the recognition helix amino acid sequences. In another embodiment, provided herein is a ZFP expression vector comprising a nucleotide sequence encoding a ZFP having one or more recognition helices.

Targeted Integration

The disclosed methods and compositions can be used to cleave DNA in any cell genome at a first insertion site, which facilitates the stable, targeted integration of an exogenous sequence into the insertion site and/or excision of exogenous sequences in the presence of the appropriate ZFN pairs. Furthermore, the DNA repair and recombination resulting from the excision of exogenous sequence produces a second insertion site that is identical to the first insertion site. Accordingly, the ZFN pairs initially used to target the first insertion site can be subsequently reused.

The disclosed methods and compositions can be used to cleave DNA in any cell genome at a first insertion site, which facilitates the stable, targeted integration of an exogenous sequence into the insertion site and/or excision of exogenous sequences in the presence of the appropriate ZFN pairs. Furthermore, the DNA repair and recombination resulting from the excision of exogenous sequence produces a second insertion site that is recognized, bound and cleaved by the site specific nuclease. Accordingly, the ZFN pairs initially used to target the first insertion site can be subsequently reused.

A further embodiment includes the introduction of an exogenous sequence comprising a marker gene and a gene of interest within a plant cell. Both the marker gene and gene of interest are flanked by the same ZFN binding sites (depicted as triangles with different shadings), so that the marker gene can be deleted as appropriate, for example when inserting additional genes. The removal of the marker gene can result in the subsequent repair of the ZFN binding site, so that the ZFN binding site is recognizable and targetable by the ZFN originally used to remove the mareker gene.

In organisms such as plants where there are a limited number of effective selectable markers, this allows the use of as few as one selectable marker gene, greatly facilitating the potential to stack genes of interest. In certain embodiments, for example depending on efficiency of homology-directed DNA repair, a "split" selectable marker may be used. Correct integration of a donor DNA sequence using a split-selectable marker creates an expressible selectable marker gene. In another embodiment, the exogenous sequence for removal is flanked in the genome by partial sequences of a split marker gene. Upon excision, the marker gene is re-constructed, resulting in the creation of a functional marker gene.

Depending on the efficiency of homology-directed DNA repair, the use of a "split" selectable marker may need to be used. Correct integration of a donor DNA sequence using a split-selectable marker creates an expressible selectable marker gene. Selectable markers can be excised from an integrated DNA sequence and can therefore be recycled. Use of selectable marker excision limits the number of selectable markers needed to two or possibly only one.

For targeted integration into an integrated insertion site as described herein, one or more DNA-binding domains (e.g., ZFPs) are engineered to bind a target site at or near the predetermined cleavage site, and a fusion protein comprising the engineered DNA-binding domain and a cleavage domain is expressed in a cell. Upon binding of the DNA-binding (e.g., zinc finger) portion of the fusion protein to the target site, the DNA is cleaved, preferably via a double-stranded break, near the target site by the cleavage domain.

The presence of a double-stranded break in the insertion site facilitates integration of exogenous sequences via homologous recombination or through non homologous end joining. In certain embodiments, the polynucleotide comprising the exogenous sequence to be inserted into the insertion site will include one or more regions of homology with the insertion site polynucleotide and/or the surrounding genome to facilitate homologous recombination. Approximately 25, 50, 100, 200, 500, 750, 1,000, 1,500, 2,000 nucleotides or more of sequence homology between a donor and a genomic sequence (or any integral value between 10 and 2,000 nucleotides, or more) will support homologous recombination therebetween. In certain embodiments, the homology arms are less than 1,000 basepairs in length. In other embodiments, the homology arms are less than 750 basepairs in length. See, also, U.S. Provisional Patent Application No. 61/124,047, which is incorporated herein by reference. A donor molecule (exogenous sequence) can contain several, discontinuous regions of homology to cellular chromatin. For example, for targeted insertion of sequences not normally present in a region of interest, said sequences can be present in a donor nucleic acid molecule and flanked by regions of homology to a gene sequence in the region of interest.

Any sequence of interest (exogenous sequence) can be introduced into or excised from an insertion site as described herein. Exemplary exogenous sequences include, but are not limited to any polypeptide coding sequence (e.g., cDNAs), promoter, enhancer and other regulatory sequences (e.g., interfering RNA sequences, shRNA expression cassettes, epitope tags, marker genes, cleavage enzyme recognition sites and various types of expression constructs. Such sequences can be readily obtained using standard molecular biological techniques (cloning, synthesis, etc.) and/or are commercially available. The exogenous sequence can be introduced into the cell prior to, concurrently with, or subsequent to, expression of the fusion protein(s).

The donor polynucleotide can be DNA or RNA, single-stranded or double-stranded and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a nanoparticle, liposome or poloxamer, or can be delivered to plant cells by bacteria or viruses (e.g., *Agrobacterium, Rhizobium* sp. NGR234, *Sinorhizoboium meliloti, Mesorhizobium loti*, tobacco mosaic virus, potato virus X, cauliflower mosaic virus and cassava vein mosaic virus. See, e.g., Chung et al. (2006) *Trends Plant Sci.* 11(1):1-4.

As detailed above, the binding sites on the insertion site for two fusion proteins (homodimers or heterodimers), each comprising a zinc finger binding domain and a cleavage half-domain, can be located from 3-5 base pairs, 5-8 base pairs or 15-18 base pairs apart, as measured from the edge of each binding site nearest the other binding site, and cleavage occurs between the binding sites. Whether cleavage occurs at a single site or at multiple sites between the binding sites is immaterial, since the cleaved genomic sequences are replaced by the donor sequences. Thus, for efficient alteration of the sequence of a single nucleotide pair by targeted recombination, the midpoint of the region between the binding sites is within 10,000 nucleotides of that nucleotide pair, preferably within 1,000 nucleotides, or 500 nucleotides, or 200 nucleotides, or 100 nucleotides, or 50 nucleotides, or 20 nucleotides, or 10 nucleotides, or 5 nucleotide, or 2 nucleotides, or one nucleotide, or at the nucleotide pair of interest.

Methods and compositions are also provided that may enhance levels of targeted recombination including, but not limited to, the use of additional ZFP-functional domain fusions to activate expression of genes involved in homologous recombination, such as, for example, plant genes of the RAD54 epistasis group (e.g., AtRad54, AtRad51), and genes whose products interact with the aforementioned gene products. See, e.g., Klutstein M, et al. *Genetics.* 2008 April; 178(4):2389-97.

Similarly ZFP-functional domain fusions can be used, in combination with the methods and compositions disclosed herein, to repress expression of genes involved in non-homologous end joining (e.g., Ku70/80, XRCC4, poly(ADP ribose) polymerase, DNA ligase 4). See, for example, Riha et al. (2002) *EMBO* 21:2819-2826; Freisner et al. (2003) *Plant J.* 34:427-440; Chen et al. (1994) *European Journal of Biochemistry* 224:135-142. Methods for activation and repression of gene expression using fusions between a zinc finger binding domain and a functional domain are disclosed, for example, in co-owned U.S. Pat. Nos. 6,534,261; 6,824,978 and 6,933,113. Additional repression methods include the use of antisense oligonucleotides and/or small interfering RNA (siRNA or RNAi) or shRNAs targeted to the sequence of the gene to be repressed.

Further increases in efficiency of targeted recombination, in cells comprising a zinc finger/nuclease fusion molecule and a donor DNA molecule, are achieved by blocking the cells in the $G_2$ phase of the cell cycle, when homology-driven repair processes are maximally active. Such arrest can be achieved in a number of ways. For example, cells can be treated with e.g., drugs, compounds and/or small molecules which influence cell-cycle progression so as to arrest cells in $G_2$ phase. Exemplary molecules of this type include, but are not limited to, compounds which affect microtubule polymerization (e.g., vinblastine, nocodazole, Taxol), compounds that interact with DNA (e.g., cis-platinum(II) diamine dichloride, Cisplatin, doxorubicin) and/or compounds that affect DNA synthesis (e.g., thymidine, hydroxyurea, L-mimosine, etoposide, 5-fluorouracil). Additional increases in recombination efficiency are achieved by the use of histone deacetylase (HDAC) inhibitors (e.g., sodium butyrate, trichostatin A) which alter chromatin structure to make genomic DNA more accessible to the cellular recombination machinery.

Additional methods for cell-cycle arrest include overexpression of proteins which inhibit the activity of the CDK cell-cycle kinases, for example, by introducing a cDNA encoding the protein into the cell or by introducing into the cell an engineered ZFP which activates expression of the gene encoding the protein. Cell-cycle arrest is also achieved by inhibiting the activity of cyclins and CDKs, for example, using RNAi methods (e.g., U.S. Pat. No. 6,506,559) or by introducing into the cell an engineered ZFP which represses expression of one or more genes involved in cell-cycle progression such as, for example, cyclin and/or CDK genes.

See, e.g., co-owned U.S. Pat. No. 6,534,261 for methods for the synthesis of engineered zinc finger proteins for regulation of gene expression.

Alternatively, in certain cases, targeted cleavage is conducted in the absence of a donor polynucleotide (preferably in S or G2 phase), and recombination occurs between homologous chromosomes.

Expression Vectors

A nucleic acid encoding one or more fusion proteins (e.g., ZFNs) as described herein can be cloned into a vector for transformation into prokaryotic or eukaryotic cells for replication and/or expression. Vectors can be prokaryotic vectors, e.g., plasmids, or shuttle vectors, insect vectors, or eukaryotic vectors. A nucleic acid encoding a fusion protein can also be cloned into an expression vector, for administration to a cell.

To express the fusion proteins (e.g., ZFNs), sequences encoding the fusion proteins are typically subcloned into an expression vector that contains a promoter to direct transcription. Suitable bacterial and eukaryotic promoters are well known in the art and described, e.g., in Sambrook et al., *Molecular Cloning, A Laboratory Manual* (2nd ed. 1989; 3$^{rd}$ ed., 2001); Kriegler, *Gene Transfer and Expression: A Laboratory Manual* (1990); and *Current Protocols in Molecular Biology* (Ausubel et al., supra. Bacterial expression systems for expressing the ZFP are available in, e.g., *E. coli, Bacillus* sp., and *Salmonella* (Palva et al., *Gene* 22:229-235 (1983)). Kits for such expression systems are commercially available. Eukaryotic expression systems for mammalian cells, yeast, and insect cells are well known by those of skill in the art and are also commercially available.

The promoter used to direct expression of a fusion protein-encoding nucleic acid depends on the particular application. For example, a strong constitutive promoter suited to the host cell is typically used for expression and purification of fusion proteins.

In contrast, when a fusion protein is administered in vivo for regulation of a plant gene (see, "Nucleic Acid Delivery to Plant Cells" section below), either a constitutive, regulated (e.g., during development, by tissue or cell type, or by the environment) or an inducible promoter is used, depending on the particular use of the fusion protein. Non-limiting examples of plant promoters include promoter sequences derived from *A. thaliana* ubiquitin-3 (ubi-3) (Callis, et al., 1990, J. Biol. Chem. 265-12486-12493); *A. tumifaciens* mannopine synthase (Amas) (Petolino et al., U.S. Pat. No. 6,730,824); and/or Cassava Vein Mosaic Virus (CsVMV) (Verdaguer et al., 1996, Plant Molecular Biology 31:1129-1139). See, also, Examples.

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to a nucleic acid sequence encoding the fusion protein, and signals required, e.g., for efficient polyadenylation of the transcript, transcriptional termination, ribosome binding sites, or translation termination. Additional elements of the cassette may include, e.g., enhancers, heterologous splicing signals, and/or a nuclear localization signal (NLS).

The particular expression vector used to transport the genetic information into the cell is selected with regard to the intended use of the fusion proteins, e.g., expression in plants, animals, bacteria, fungus, protozoa, etc. (see expression vectors described below). Standard bacterial and animal expression vectors are known in the art and are described in detail, for example, U.S. Patent Publication 20050064474A1 and International Patent Publications WO05/084190, WO05/014791 and WO03/080809.

Standard transfection methods can be used to produce bacterial, mammalian, yeast or insect cell lines that express large quantities of protein, which can then be purified using standard techniques (see, e.g., Colley et al., *J. Biol. Chem.* 264:17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds., 1983).

Any of the well known procedures for introducing foreign nucleotide sequences into such host cells may be used. These include the use of calcium phosphate transfection, polybrene, protoplast fusion, electroporation, ultrasonic methods (e.g., sonoporation), liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

Delivery to Plant Cells

As noted above, DNA constructs may be introduced into (e.g., into the genome of) a desired plant host by a variety of conventional techniques. For reviews of such techniques see, for example, Weissbach & Weissbach *Methods for Plant Molecular Biology* (1988, Academic Press, N.Y.) Section VIII, pp. 421-463; and Grierson & Corey, *Plant Molecular Biology* (1988, 2d Ed.), Blackie, London, Ch. 7-9.

For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al. (1987) *Nature* 327:70-73). Alternatively, the DNA construct can be introduced into the plant cell via nanoparticle transformation (see, e.g., U.S. patent application Ser. No. 12/245,685, which is incorporated herein by reference in its entirety). Alternatively, the DNA constructs may be combined with suitable T-DNA border/flanking regions and introduced into a conventional *Agrobacterium tumefaciens* host vector. *Agrobacterium tumefaciens*-mediated transformation techniques, including disarming and use of binary vectors, are well described in the scientific literature. See, for example Horsch et al. (1984) *Science* 233:496-498, and Fraley et al. (1983) *Proc. Nat'l. Acad. Sci. USA* 80:4803.

In addition, gene transfer may be achieved using non-Agrobacterium bacteria or viruses such as *Rhizobium* sp. NGR234, *Sinorhizoboium meliloti, Mesorhizobium loti*, potato virus X, cauliflower mosaic virus and cassava vein mosaic virus and/or tobacco mosaic virus, See, e.g., Chung et al. (2006) *Trends Plant Sci.* 11(1):1-4.

The virulence functions of the *Agrobacterium tumefaciens* host will direct the insertion of a T-strand containing the construct and adjacent marker into the plant cell DNA when the cell is infected by the bacteria using binary T DNA vector (Bevan (1984) *Nuc. Acid Res.* 12:8711-8721) or the co-cultivation procedure (Horsch et al. (1985) *Science* 227:1229-1231). Generally, the *Agrobacterium* transformation system is used to engineer dicotyledonous plants (Bevan et al. (1982) *Ann. Rev. Genet* 16:357-384; Rogers et al. (1986)

*Methods Enzymol.* 118:627-641). The *Agrobacterium* transformation system may also be used to transform, as well as transfer, DNA to monocotyledonous plants and plant cells. See U.S. Pat. No. 5,591,616; Hernalsteen et al. (1984) *EMBO J* 3:3039-3041; Hooykass-Van Slogteren et al. (1984) *Nature* 311:763-764; Grimsley et al. (1987) *Nature* 325:1677-179; Boulton et al. (1989) *Plant Mol. Biol.* 12:31-40; and Gould et al. (1991) *Plant Physiol.* 95:426-434.

Alternative gene transfer and transformation methods include, but are not limited to, protoplast transformation through calcium-, polyethylene glycol (PEG)- or electroporation-mediated uptake of naked DNA (see Paszkowski et al. (1984) *EMBO J* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276) and electroporation of plant tissues (D'Halluin et al. (1992) *Plant Cell* 4:1495-1505). Additional methods for plant cell transformation include microinjection, silicon carbide mediated DNA uptake (Kaeppler et al. (1990) *Plant Cell Reporter* 9:415-418), and microprojectile bombardment (see Klein et al. (1988) *Proc. Nat. Acad. Sci. USA* 85:4305-4309; and Gordon-Kamm et al. (1990) *Plant Cell* 2:603-618).

The disclosed methods and compositions can be used to insert exogenous sequences into the insertion site that has been inserted into the genome of a plant cell. This is useful inasmuch as expression of an introduced transgene into a plant genome depends critically on its integration site. Accordingly, genes encoding, e.g., herbicide tolerance, insect resistance, nutrients, antibiotics or therapeutic molecules can be inserted, by targeted recombination, into regions of a plant genome favorable to their expression.

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillian Publishing Company, New York, 1983; and Binding, *Regeneration of Plants, Plant Protoplasts*, pp. 21-73, CRC Press, Boca Raton, 1985. Regeneration can also be obtained from plant callus, explants, organs, pollens, embryos or parts thereof. Such regeneration techniques are described generally in Klee et al. (1987) *Ann. Rev. of Plant Phys.* 38:467-486.

Nucleic acids introduced into a plant cell can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yarn), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera *Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna,* and *Zea*.

One of skill in the art will recognize that after the exogenous sequence is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the β-glucuronidase, luciferase, B or C1 genes) that may be present on the recombinant nucleic acid constructs. Such selection and screening methodologies are well known to those skilled in the art.

Physical and biochemical methods also may be used to identify plant or plant cell transformants containing inserted gene constructs. These methods include but are not limited to: 1) Southern analysis or PCR amplification for detecting and determining the structure of the recombinant DNA insert; 2) Northern blot, 51 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays (ELISA), where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, northern blots of the RNA (e.g., mRNA) isolated from the tissues of interest. Typically, if the mRNA is present or the amount of mRNA has increased, it can be assumed that the corresponding transgene is being expressed. Other methods of measuring gene and/or encoded polypeptide activity can be used. Different types of enzymatic assays can be used, depending on the substrate used and the method of detecting the increase or decrease of a reaction product or by-product. In addition, the levels of polypeptide expressed can be measured immunochemically, i.e., ELISA, RIA, EIA and other antibody based assays well known to those of skill in the art, such as by electrophoretic detection assays (either with staining or western blotting). As one non-limiting example, the detection of the AAD-1 and PAT proteins using an ELISA assay is described in U.S. patent application Ser. No. 11/587,893 which reference is hereby incorporated by reference in its entirety herein. The transgene may be selectively expressed in some tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed has the transgene or gene construct. The present disclosure further encompasses the progeny, clones, cell lines or cells of the transgenic plants described above wherein said progeny, clone, cell line or cell has the transgene or gene construct.

Fusion proteins (e.g., ZFNs) and expression vectors encoding fusion proteins can be administered directly to the plant for gene regulation, targeted cleavage, and/or recombination. In certain embodiments, the plant contains multiple paralogous target genes. It is known that plants may contain multiple paralogous genes. Thus, one or more different fusion proteins or expression vectors encoding fusion proteins may be administered to a plant in order to target one or more Zp15 genes in the plant.

Administration of effective amounts is by any of the routes normally used for introducing fusion proteins into ultimate contact with the plant cell to be treated. The ZFPs are administered in any suitable manner, preferably with acceptable carriers. Suitable methods of administering such modulators are available and well known to those of skill in the art, and, although more than one route can be used to administer a particular composition, a particular route can often provide a more immediate and more effective reaction than another route.

Carriers may also be used and are determined in part by the particular composition being administered, as well as by the particular method used to administer the composition. Accordingly, there is a wide variety of suitable formulations of carriers that are available.

Delivery to Mammalian Cells

The ZFNs described herein may be delivered to a target mammalian cell by any suitable means, including, for example, by injection of ZFN mRNA. See, Hammerschmidt et al. (1999) *Methods Cell Biol.* 59:87-115

Methods of delivering proteins comprising zinc-fingers are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

ZFNs as described herein may also be delivered using vectors containing sequences encoding one or more of the ZFNs. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more ZFN encoding sequences. Thus, when one or more pairs of ZFNs are introduced into the cell, the ZFNs may be carried on the same vector or on different vectors. When multiple vectors are used, each vector may comprise a sequence encoding one or multiple ZFNs.

Conventional viral and non-viral based gene transfer methods can be used to introduce nucleic acids encoding engineered ZFPs into mammalian cells. Such methods can also be used to administer nucleic acids encoding ZFPs to mammalian cells in vitro. In certain embodiments, nucleic acids encoding ZFPs are administered for in vivo or ex vivo uses.

Non-viral vector delivery systems include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids. Viral vector delivery systems include DNA and RNA viruses, which have either episomal or integrated genomes after delivery to the cell. Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386, 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration). The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946, 787).

As noted above, the disclosed methods and compositions can be used in any type of mammalian cell. The proteins (e.g., ZFPs), polynucleotides encoding same and compositions comprising the proteins and/or polynucleotides described herein may be delivered to a target cell by any suitable means. Suitable cells include but are not limited to eukaryotic and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NSO, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces*, *Pichia* and *Schizosaccharomyces*. In certain embodiments, the cell line is a CHO-K1, MDCK or HEK293 cell line. Suitable primary cells include peripheral blood mononuclear cells (PBMC), and other blood cell subsets such as, but not limited to, CD4+ T cells or CD8+ T cells. Suitable cells also include stem cells such as, by way of example, embryonic stem cells, induced pluripotent stem cells, hematopoietic stem cells, neuronal stem cells and mesenchymal stem cells.

Embodiments of the subject disclosure are further exemplified in the following Examples. It should be understood that these Examples are given by way of illustration only. From the above embodiments and the following Examples, one skilled in the art can ascertain the essential characteristics of this disclosure, and without departing from the spirit and scope thereof, can make various changes and modifications of the embodiments of the disclosure to adapt it to various usages and conditions. Thus, various modifications of the embodiments of the disclosure, in addition to those shown and described herein, will be apparent to those skilled in the art from the foregoing description. Such modifications are also intended to fall within the scope of the appended claims. The following is provided by way of illustration and not intended to limit the scope of the invention.

EXAMPLES

Example 1: Design and Construction of pDAB105826

The plasmid of pDAB105826 containing a first zinc finger nuclease gene expression cassette and a second pat gene expression cassette was designed and constructed using art recognized protocols. The resulting first zinc finger nuclease gene expression cassette contained the following gene elements; the *Zea mays* Ubiquitin1 promoter (ZmUbi1; U.S. Pat. No. 7,179,902):: the coding sequence to the zinc finger nuclease gene that recognizes and cleaves eZFN2 (eZFN2; U.S. Pat. No. 8,802,921):: the *Zea mays* Per 5 3UTR (ZmPer5; U.S. Pat. No. 6.699.984). The second pat gene expression cassette contained the following gene elements; the rice actin promoter (OsAct1; U.S. Pat. No. 5,641,876):: the phosphinothricin acetyltransferase gene (pat; U.S. Pat. No. RE44962):: and the *Zea mays* lipase 3' UTR (ZmLip; U.S. Pat. No. 7,179,902). The assembly of this plasmid was confirmed via restriction enzyme digestion and sequencing reactions and is provided as FIG. 1.

Example 2: Design and Construction of pDAB118231

Figure 2:
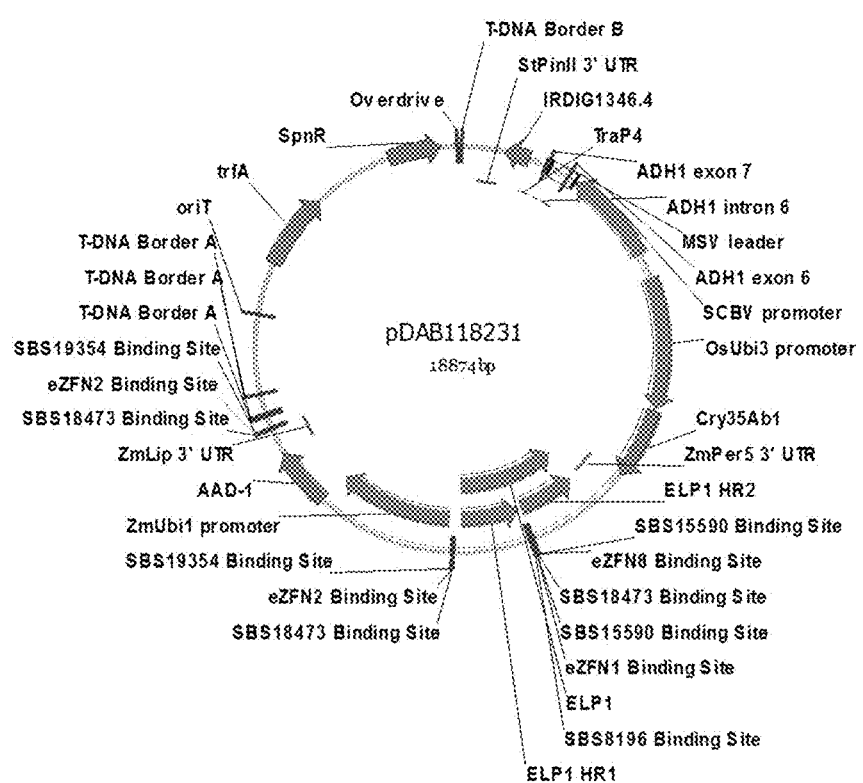
FIG. 2 is a schematic depicting a plasmid map of pDAB118231.

The plasmid of pDAB118231 contained a first cry34 gene expression cassette, a second cry35Ab1 gene expression cassette, an engineered landing pad (ELP1; U.S. Pat. No. 2014/0090113), a first site specific nuclease binding site (eZFN2 Binding Site; SEQ ID NO:1), a third aad-1 gene expression cassette, and a second site specific nuclease binding site (eZFN2 Binding Site) was designed and constructed using art recognized protocols. The eZFN2 binding sites and the aad-1 gene expression cassette are provided as SEQ ID NO:18. The resulting first cry34 gene expression cassette contained the following gene elements; the sugarcane bacilliform virus promoter (SCBV; Bouhida et al., J. Gen. Virol. 74:15-22 (1993)):: the TRAP 4 chloroplast transit peptide (TRAP4; U.S. Pat. App. No. 2013/0295638):: the coding sequence to the cry34 transgene (Cry34; U.S. Pat. No. 7,524,810; the TRAP4-cry34Ab1 sequence is provided as SEQ ID NO:19):: the *Solanum tuberosum* pinII 3'UTR (StPinII; An et al., Plant Cell. 1; 115-22 (1989)). The second cry35Ab1 gene expression cassette contained the following gene elements; the rice ubiquitin 3 promoter (OsUbi3; Sivarnani, E., Qu, R., Plant Molecular Biology 60; 225-239 (2006)):: the cry35Ab1 transgene (Cry35Ab1; U.S. Pat. No. 7,985,892):: and the *Zea mays* per 5 3' UTR (ZmPer5; U.S. Pat. No. 6,699,984). The third aad-1 transgene expression cassette contained the following gene elements; the *Zea mays* Ubiquitin 1 promoter (ZmUbi1; U.S. Pat. No. 7,179,902):: the aad-1 transgene (AAD-1; U.S. Pat. App. No. 2009/0093366):: and the *Zea mays* lipase 3' UTR (ZmLip; U.S. Pat. No. 7,179,902). The assembly of this plasmid was confirmed via restriction enzyme digestion and sequencing reactions and is provided as FIG. 2.

Example 3: Design and Construction of pDAB118232

Figure 3:
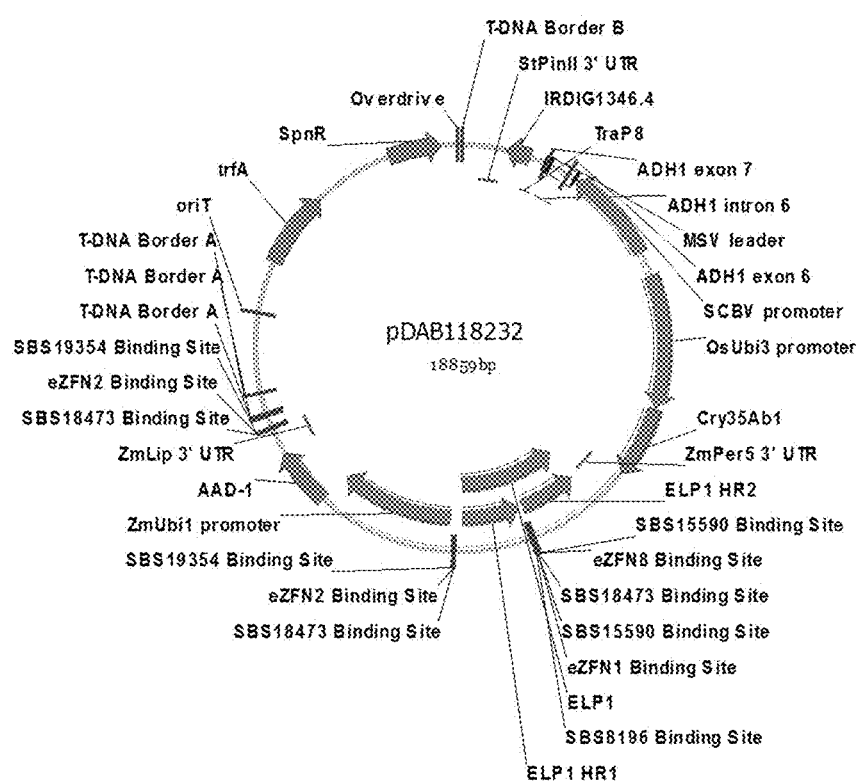
FIG. 3 is a schematic depicting a plasmid map of pDAB118232.

The plasmid of pDAB118232 contained a first cry34 gene expression cassette, a second cry35Ab1 gene expression cassette, an engineered landing pad (ELP1; U.S. Pat. No. 2014/0090113), a first site specific nuclease binding site (eZFN2 Binding Site), a third aad-1 gene expression cassette, and a second site specific nuclease binding site (eZFN2 Binding Site) was designed and constructed using art recognized protocols. The eZFN2 binding sites and the aad-1 gene expression cassette are provided as SEQ ID NO:18. The resulting first cry34 gene expression cassette contained the following gene elements; the sugarcane bacilliform virus promoter (SCBV; Bouhida et al., J. Gen. Virol. 74:15-22 (1993)):: the TRAP 8 chloroplast transit peptide (TRAP8; Int'l. Pat. App. No. 2013/158766):: the coding sequence to the cry34 transgene (Cry34; U.S. Pat. No. 7,524,810; the TRAP8-cry34Ab1 sequence is provided as SEQ ID NO:20):: the *Solanum tuberosum* pinII 3'UTR (StPinII; An et al., Plant Cell. 1; 115-22 (1989)). The second cry35Ab1 gene expression cassette contained the following gene elements; the rice Ubiquitin 3 promoter (OsUbi3; Sivamani, E., Qu. R., Plant Molecular Biology 60; 225-239 (2006)):: the cry35Ab1 transgene (Cry35Ab 1; U.S. Pat. No. 7,985,892):: and the *Zea mays* per 5 3' UTR (ZmPer5; U.S. Pat. No. 6,699,984). The third aad-1 transgene expression cassette contained the following gene elements; the *Zea mays* Ubiquitin 1 promoter (ZmUbi1; U.S. Pat. No. 7,179, 902):: the aad-1 transgene (AAD-1; U.S. Pat. App. No. 2009/0093366):: and the *Zea mays* lipase 3' UTR (ZmLip; U.S. Pat. No. 7,179,902). The assembly of this plasmid was confirmed via restriction enzyme digestion and sequencing reactions and is provided as FIG. 3.

Example 4: Design and Construction of pDAB118233

Figure 4:
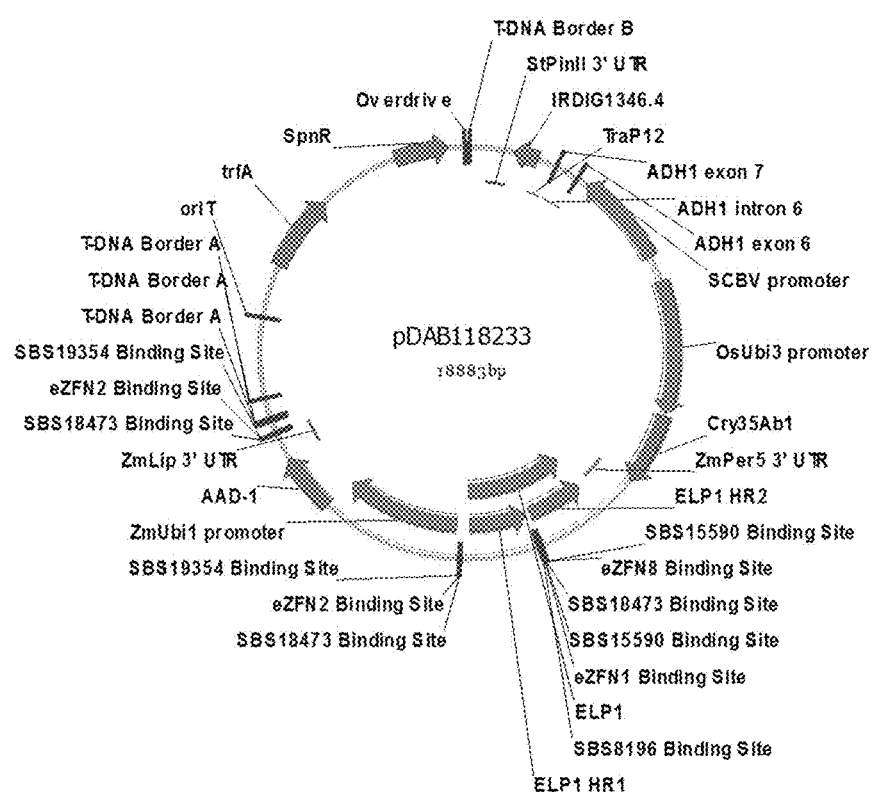
FIG. 4 is a schematic depicting a plasmid map of pDAB118233.

The plasmid of pDAB118233 contained a first cry34 gene expression cassette, a second cry35Ab1 gene expression cassette, an engineered landing pad (ELP1; U.S. Pat. No. 2014/0090113), a first site specific nuclease binding site (eZFN2 Binding Site), a third aad-1 gene expression cassette, and a second site specific nuclease binding site (eZFN2 Binding Site) was designed and constructed using art recognized protocols. The eZFN2 binding sites and the aad-1 gene expression cassette are provided as SEQ ID NO:18. The resulting first cry34 gene expression cassette contained the following gene elements; the sugarcane bacilliform virus promoter (SCBV; Bouhida et al., J. Gen. Virol. 74:15-22 (1993)):: the TRAP 12 chloroplast transit peptide (TRAP12; U.S. Pat. App. No. 2013/0205440):: the coding sequence to the cry34 transgene (Cry34; U.S. Pat. No. 7,524,810; the TRAP 12-cry34Ab1 sequence is provided as SEQ ID NO:21):: the *Solanum tuberosum* pinII 3'UTR (StPinII; An et al., Plant Cell. 1; 115-22 (1989)). The second ery35Ab1 gene expression cassette contained the following gene elements; the rice ubiquitin 3 promoter (OsUbi3; Sivaniani, E., Qu, R., Plant Molecular Biology 60; 225-239 (2006)):: the ery35Ab1 transgene (Cry35Ab 1; U.S. Pat. No. 7,985,892):: and the *Zea mays* per 5 3' UTR (ZmPer5; U.S. Pat. No. 6,699,984). The third aad-1 transgene expression cassette contained the following gene elements; the *Zea mays* Ubiquitin 1 promoter (ZmUbi1; U.S. Pat. No. 7,179, 902):: the aad-1 transgene (AAD-1; U.S. Pat. App. No. 2009/0093366):: and the *Zea mays* lipase 3' UTR (ZmLip; U.S. Pat. No. 7,179,902). The assembly of this plasmid was confirmed via restriction enzyme digestion and sequencing reactions and is provided as FIG. 4.

Example 5: Plant Transformation and Molecular Confirmation of Transgenic Events

The above constructs were introduced into the transformation line of *Zea mays* c.v. B104 using *Agrobacterim-* based transformation. The experimental constructs were transformed into maize via *Agrobacterium*-mediated transformation of immature embryos isolated from the inbred line *Zea mays* c.v. B104. The method used was similar to those published by Ishida et al. (1996) Nature Biotechnol 14:745-750 and Frame et al. (2006) Plant Cell Rep 25: 1024-1034, but with several modifications and improvements as described in Miller (2013) WO 2013090734 A1 to make the method amenable to high-throughput transformation in an industrial setting. An example of a method used to produce a number of transgenic events in maize is given in U.S. Pat. App. Pub. No. US 2013/0157369 A1, beginning with the embryo infection and co-cultivation steps.

Based on qPCR assays, T0 events that were determined to contain 1-2 copies of all components of the transgene and lacking detectable plasmid backbone were retained for $T_1$ seed production. $T_0$ events were reciprocally backcrossed to *Zea mays* c.v. B104 to produce the $T_1$ generation. Three events per construct were selected for the present study.

Example 6: $T_1$ Plant Evaluation and Crossing

Seed from the resulting T1Target progeny lines (segregating 1:1 null: hemizygous) produced from the parental target plants lines of the construct pDAB118231, pDAB118232 and pDAB118233 containing the transgenic events (118231[1]-016.001, 118231[1]-021.001, 118231[1]-028.001, 118232[1]-002.001, 118232[1]-023.001, 118232[1]-028.001, 118233[1]-006.001, 118233[1]-011.001, 118233[1]-015.001) were planted and grown in a greenhouse. Additionally, S1 seeds from the eZFN2 expressing line pDAB105826.2.137 (segregating 1:2:1 null: hemizygous:homozygous) were planted in the greenhouses and grown. At approximately the V2 leaf stage, these events were treated with the herbicide that matched their respective selectable markers; events with the aad1 transgene were treated with Assure II™ at 184 g ae/ha+1% crop oil concentrate, events with the pat transgene were treated with Ignite™ 280 SL (glufosinate) (480 g ae/ha) to remove null plants that did not possess a transgene. Surviving plants were genotyped for zygosity using molecular confirmation assays. The eZFN2 expressing plants containing the event (pDAB105826.2.137) were crossed to the target plants containing the events (118231[1]-016.001, 118231[1]-021.001, 118231[1]-028.001, 118232[1]-002.001, 118232[1]-023.001, 118232[1]-028.001, 118233[1]-006.001, 118233[1]-011.001, 118233[1]-015.001) to create F1 breeding stacks for genome editing evaluation. Crosses were made so that pollen was isolated from the eZFN2 expressing plants (preferably homozygous plants) and used to fertilize the T1 target plants which contained the transgene.

Example 7: Molecular Analysis of the Events Containing an Excised AAD-1 Transgene The F1 breeding stacks resulting from T1 Targets of the construct pDAB118231, pDAB118232 and pDAB118233× eZFN2 expressing line pDAB105826.2.137 were planted in the greenhouse. One week after planting, the plants were sampled for DNA according to the standard protocols. Briefly, a couple of 1 cm leaf disks were collected from each plant for molecular analysis. DNA was extracted using the Qiagen MagAttract™ kit (Qiagen, Germantown, Mass.) on Thermo KingFisherFlex™ robot (Thermo Scientific, Inc., Carlsbad, Calif.). Copy number analysis was performed using specific TaqMan® assays for the aad-1 transgene, ELP, cry35Ab1 transgene, and pat transgene. Biplex TaqMan® PCR reactions were set up according to Table 1 and performed using the thermocycler conditions in Table 2 and the primers listed in Table 3. The level of fluorescence generated for each reaction was analyzed using the Roche LightCycler480™ Real-Time PCR system according to the manufacturer's recommendations. The FAM fluorescent moiety was excited at an optical density of 465/510 nm, and the HEX fluorescent moiety was excited at an optical density of 533/580 nm. The copy number were determined by comparison of Target/Reference values (ΔΔCt) for unknown samples (output by the LightCycler480™) to Target/Reference values (ΔΔCt) of known copy number standards (1-Copy: hemizygous, 2-Copy: homozygous). After molecular confirmation of the transgenic events was completed, plants that contained modified events of an excised aad-1 selectable marker were identified and grown to maturity. These plants were crossed (excised plants used as pollen donors) to *Zea mays* c.v. B104 plants to produce seed.

TABLE 1

| PCR Reaction Buffer | | |
| --- | --- | --- |
| Number of Reactions | μl each | Final Concentration |
| H₂O | 0.5 μL | |
| PVP (10%) | 0.1 μL | 0.1% |
| ROCHE 2X Master Mix | 5 μL | 1X |
| GOI Forward Primer (10 μM) | 0.4 μL | 0.4 μM |
| GOI Reverse Primer (10 μM) | 0.4 μL | 0.4 μM |
| GOI Probe (5 μM) | 0.4 μL | 0.2 μM |
| Invertase Forward Primer (10 μM) | 0.4 μL | 0.4 μM |
| Invertase Reverse Primer (10 μM) | 0.4 μL | 0.4 μM |
| Invertase Probe (5 μM) | 0.4 μL | 0.2 μM |

TABLE 2

| PCR Reaction Conditions | | | |
| --- | --- | --- | --- |
| PCR Steps | Temp (° C.) | Time | No. of cycles |
| Step-1 | 95 | 10 minutes | 1 |
| Step-2 | 95 | 10 seconds | 40 |
| | 58 | 35 seconds | |
| | 72 | 1 second | |
| Step-3 | 40 | 10 seconds | 1 |

TABLE 3

| Primers used for DNA Analysis | | | |
| --- | --- | --- | --- |
| Oligo Name | Oligo Sequence | Gene/ Sequence of interest | Fluorophore/ Quencher |
| Cry35Ab1 F | SEQ ID NO: 2 TGACACAAAGCTGAAAGACTAT | cry35Ab1 | 6FAM/IowaBlack/ Zen |

TABLE 3-continued

Primers used for DNA Analysis

| Oligo Name | Oligo Sequence | Gene/Sequence of interest | Fluorophore/Quencher |
|---|---|---|---|
| Cry35Ab1 R | SEQ ID NO: 3 TTGAGGATGTAGTAAGGAGTGG | | |
| Cry35Ab1 P | SEQ ID NO: 4 ACGCTGGTGCCGTGTAT | | |
| AAD1 F | SEQ ID NO: 5 TGTTCGGTTCCCTCTACCAA | aad-1 | 6FAM/MGB |
| AAD1 R | SEQ ID NO: 6 CAACATCCATCACCTTGACTGA | | |
| AAD1 P | SEQ ID NO: 7 CACAGAACCGTCGCTTCAGCAACA | | |
| ELP Left F | SEQ ID NO: 8 TGGTTATGACAGGCTCCGTTTA | ELP1 | 6FAM/MGB |
| ELP Left R | SEQ ID NO: 9 AACAAACCTCCTGGCTACTTCAA | | |
| ELP Left P | SEQ ID NO: 10 CTTGCTGGTGTTATGTG | | |
| PAT F | SEQ ID NO: 11 ACAAGAGTGGATTGATGATCTAGAGAGGT | pat | Cy5/IowaBlack |
| PAT R | SEQ ID NO: 12 CTTTGATGCCTATGTGACACGTAAACAGT | | |
| PAT P | SEQ ID NO: 13 GGTGTTGTGGCTGGTATTGCTTACGCTGG | | |
| Invertase F | SEQ ID NO: 14 TGGCGGACGACGACTTGT | invertase | HEX/BHQ |
| Invertase R | SEQ ID NO: 15 AAAGTTTGGAGGCTGCCGT | | |
| Invertase P | SEQ ID NO: 16 CGAGCAGACCGCCGTGTACTT | | |

Example 8: Calculation of Rates of Excision of the Selectable Marker from the Molecular Stack Locus To determine the rate of excision of the selectable marker from a molecular stack locus containing cry34Ab1 and cry35Ab1, tissue samples from F1 plants resulting from the cross of T1 target plants by the eZFN2 expressing line were analyzed at the DNA level. To begin, a total of 1,832 F1 samples, representing 9 crosses were genotyped for removal of the aad-1 transgene using TaqMan® PCR assays for presence and copy number of component of the locus. Copy number was calculated as a ratio of ΔΔCt values of experimental lines to known standards where a ratio of two, one, or zero indicated homozygous, hemizygous, or null respectively. Since many of the crosses were made using plants that were hemizygous for target events and it was not possible to select against nulls, it was not surprising that 643 samples were identified as null for all of the gene expression cassettes found in the target events. In addition, the selectable marker gene, pat, was assayed and it was found to be missing in 248 of the plants. Additionally, there were a total of 350 plants which did not contain either the target events or the eZFN2 expressing line. None of these samples (null, without eZFN2 expressing line and without target) were included in additional analysis. From the remaining plant samples, 23 plants were found not to have any detectable copy of the aad-1 gene according to the assay, thereby resulting in an overall rate of excision of 3.7%. The excision rates ranged from 0.0-9.7% on an individual event basis with a median rate of excision among the events of 3.3%.

To examine the precision of aad-1 excision, the F1 tissue samples tested above were genotyped at additional loci within the molecular stack. Using PCR, the samples were genotyped for the presence of both cry35Ab1 and the ExZACT™ Landing Pad (ELP). It is thought that excision occurs when the plant repairs the double strand break introduced in the genome by the ZFN. Since there is no donor DNA in these experiments, two possible means of repair could be using single-stranded annealing (SSA) or non-homologous end jointing (NHEJ). Further studies were completed to investigate the heritability of gene removal and analyze the DNA footprint where excision had occurred.

TABLE 4

Results of DNA Analysis

| Cross | Generation | No. Excised AAD1 | % Excised | No. without excision | No. Analyzed with target/excisor | No. without target | No. without eZFN2 Line | No. without plant | No. Null plants | Total Analyzed |
|---|---|---|---|---|---|---|---|---|---|---|
| pDAB105826.2.137.1:: pDAB118231.1.16.1 | F1 | 1 | 1.30% | 78 | 79 | 96 | 26 | 9 | 30 | 201 |
| pDAB105826.2.137.1:: pDAB118231.1.21.1 | F1 | 3 | 2.60% | 111 | 114 | 122 | — | 4 | — | 236 |
| pDAB105826.2.137.1:: pDAB118231.1.28.1 | F1 | 1 | 1.00% | 95 | 96 | 101 | 1 | 42 | — | 198 |

TABLE 4-continued

Results of DNA Analysis

| Cross | Generation | No. Excised AAD1 | % Excised | No. without excision | No. Analyzed with target/ excisor | No. without target | No. without eZFN2 Line | No. without plant | No. Null plants | Total Analyzed |
|---|---|---|---|---|---|---|---|---|---|---|
| pDAB105826.2.137.1:: pDAB118232.1.2.1 | F1 | 4 | 7.10% | 52 | 56 | 61 | — | 35 | — | 117 |
| pDAB105826.2.137.1:: pDAB118232.1.23.1 | F1 | 0 | 0.00% | 59 | 59 | 58 | — | 19 | — | 117 |
| pDAB105826.2.137.1:: pDAB118232.1.28.1 | F1 | 7 | 9.70% | 65 | 72 | 67 | 108 | 24 | 133 | 380 |
| pDAB105826.2.137.1:: pDAB118233.1.11.1 | F1 | 4 | 5.00% | 76 | 80 | 60 | 37 | 29 | 44 | 221 |
| pDAB105826.2.137.1:: pDAB118233.1.15.1 | F1 | 1 | 3.30% | 29 | 30 | 38 | 37 | 59 | 76 | 181 |
| pDAB105826.2.137.1:: pDAB118233.1.6.1 | F1 | 2 | 5.70% | 33 | 35 | 40 | 39 | 49 | 67 | 181 |
| Project Totals | | 23 | 3.70% | 598 | 621 | 643 | 248 | 270 | 350 | 1832 |

Example 9: Analysis of Excision Events of Selectable Marker

To examine the precision of the nuclease mediated excision as well as the heritability of modification, BC1 populations of lines that were determined to be modified by the site specific nuclease in the F1 generation were planted in the Indianapolis greenhouse and evaluated for zygosity, protein expression, and DNA sequence. Heritability of site specific nuclease modification was confirmed in BC1 populations by using qPCR to genotype for the presence of cry35Ab1, cry34Ab1, and the ExZACT™ Landing Pad (ELP) (Table 3 above). These data indicate that modifications characterized in the F1 population (aad-1 had been removed) are highly heritable and segregate as expected in a BC1 population. In total 20 lines were tested and all but six of the crosses passed Chi square testing. Four of the crosses that fail Chi square testing are from the same stack (Table 5). All of the crosses T1 Target Line×eZFN2 expressing line yielded one aad-1 excised plant with the exception of only one crossing pair. Events were also screened for the presence of the eZFN2 expressing line by running the pat qPCR assay. BC1 generation qPCR results confirmed 17 of the 20 lines evaluated had no detectable aad-1 transgene present.

To examine the repair mechanism used during aad-1 excision, the fragments amplified from the lines above were sequenced and compared to their parent constructs. One plant from each of the 17 crosses was tested. In total, 15 fragments from the crosses yielded usable sequencing data, with one line yielding no PCR product and one yielding unreliable sequencing data. Sequence analysis indicates 10 of the lines resulted in perfect sequence repair following aad-1 excision (FIG. 6 and Table 6). Five lines contain small deletions and insertions which destroy the zinc finger recognition sites prior to ligation, thereby preventing further cutting (Table 6).

Figure 5:
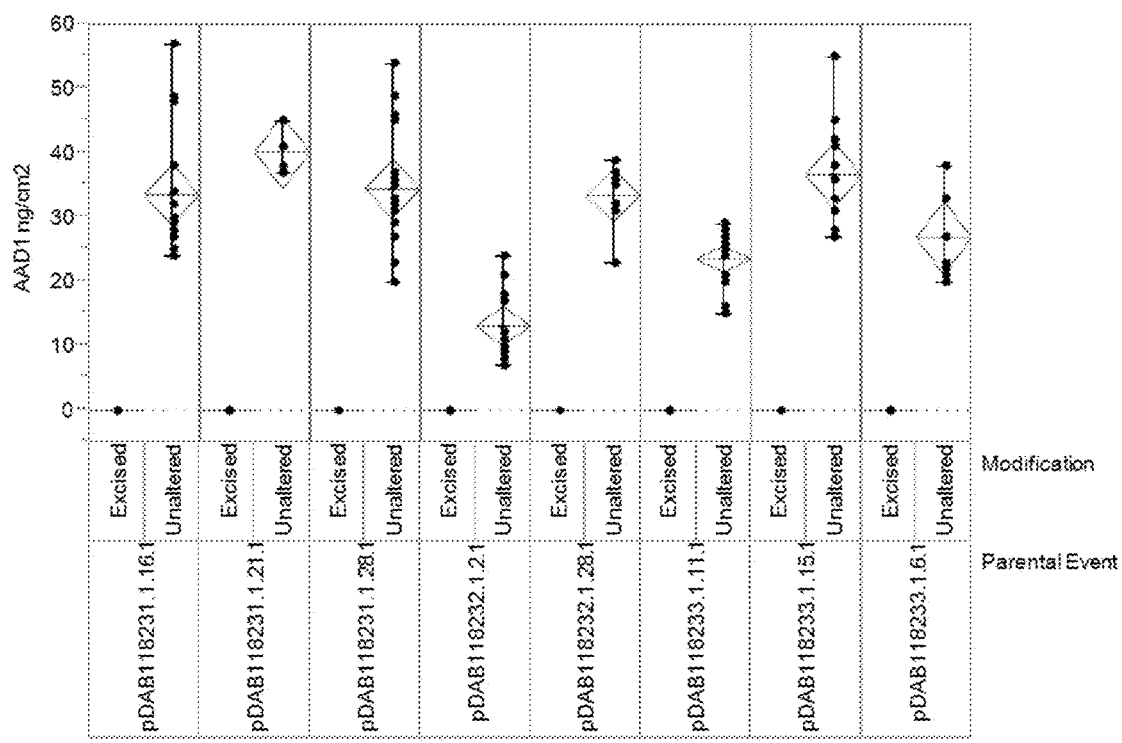
FIG. 5 is a graph depicting the AAD-1 protein quantitation in leaf tissue by event and type (i.e., excised as compare to non-excised control).

Plants exhibiting complete excision of the aad-1 gene cassette as confirmed by DNA zygosity analysis predictably contained no detectable levels of AAD-1 protein (FIG. 5). AAD-1 protein was not found in any excised plants, while protein levels between target events varied from ~5-60 ng/cm$^2$ across events.

The use of site specific nucleases allow for the capability to alter plant genomes. As shown in these Examples, frequency of selectable marker removal of 3.7%. The excision was subsequently inherited in the next generations. Further demonstrated for the first time is the gene removal and perfect DNA repair in 10 crosses out of 17 cross events (59%) through sequence level confirmation validation.

TABLE 5

DNA analysis results and chi square testing of aad-1 excision and not excised/null

| Event/Cross Name | Generation | # missing or failed qPCR reaction | # Rows | # Null | # Excised AAD1 with Excisor present | # Excised AAD1- No Excisor Present |
|---|---|---|---|---|---|---|
| pDAB118231{1}016.001 | — | 2 | 30 | 11 | — | — |
| pDAB118231{1}021.001 | — | 1 | 30 | 25 | — | — |
| pDAB118231{1}028.001 | — | 1 | 30 | 11 | — | — |
| pDAB118232{1}002.001 | — | 1 | 30 | 15 | — | — |
| pDAB118232{1}023.001 | — | 0 | 30 | 25 | — | — |
| pDAB118232{1}028.001 | — | 2 | 30 | 19 | — | — |
| pDAB118233{1}011.001 | — | 0 | 30 | 11 | — | — |
| pDAB118233{1}015.001 | — | 1 | 30 | 17 | — | — |
| pDAB118233{1}006.001 | — | 3 | 30 | 17 | — | — |
| Summary Controls | — | 11 | 270 | 151 | — | — |
| pDAB105826.2.137.1::pDAB118231.1.16.1 = 2528 | BC1 | 4 | 40 | 2 | 1 | 22 |
| pDAB105826.2.137.1::pDAB118231.1.21.1 = 2521 | BC1 | 5 | 40 | 8 | 8 | 12 |
| pDAB105826.2.137.1::pDAB118231.1.21.1 = 2522 | BC1 | 2 | 40 | 11 | 5 | 12 |
| pDAB105826.2.137.1::pDAB118231.1.21.1 = 2523 | BC1 | 4 | 40 | 7 | 10 | 10 |
| pDAB105826.2.137.1::pDAB118231.1.28.1 = 2529 | BC1 | 0 | 40 | 15 | 11 | 12 |

TABLE 5-continued

DNA analysis results and chi square testing of aad-1 excision and not excised/null

| | | | | | | |
|---|---|---|---|---|---|---|
| pDAB105826.2.137.1::pDAB118232.1.2.1 = 2524 | BC1 | 1 | 40 | 2 | 2 | 17 |
| pDAB105826.2.137.1::pDAB118232.1.2.1 = 2525 | BC1 | 3 | 40 | 0 | 2 | 26 |
| pDAB105826.2.137.1::pDAB118232.1.2.1 = 2526 | BC1 | 9 | 40 | 0 | 2 | 19 |
| pDAB105826.2.137.1::pDAB118232.1.28.1 = 2534 | BC1 | 1 | 40 | 9 | 3 | 0 |
| pDAB105826.2.137.1::pDAB118232.1.28.1 = 2535 | BC1 | 2 | 40 | 10 | 1 | 0 |
| pDAB105826.2.137.1::pDAB118232.1.28.1 = 2536 | BC1 | 2 | 40 | 21 | 0 | 0 |
| pDAB105826.2.137.1::pDAB118232.1.28.1 = 2537 | BC1 | 11 | 40 | 16 | 4 | 5 |
| pDAB105826.2.137.1::pDAB118232.1.28.1 = 2538 | BC1 | 12 | 40 | 12 | 3 | 8 |
| pDAB105826.2.137.1::pDAB118233.1.11.1 = 2539 | BC1 | 3 | 40 | 11 | 12 | 10 |
| pDAB105826.2.137.1::pDAB118233.1.11.1 = 2540 | BC1 | 16 | 40 | 7 | 9 | 4 |
| pDAB105826.2.137.1::pDAB118233.1.11.1 = 2541 | BC1 | 10 | 40 | 11 | 6 | 6 |
| pDAB105826.2.137.1::pDAB118233.1.11.1 = 2542 | BC1 | 12 | 40 | 2 | 8 | 17 |
| pDAB105826.2.137.1::pDAB118233.1.15.1 = 2543 | BC1 | 1 | 40 | 2 | 7 | 14 |
| pDAB105826.2.137.1::pDAB118233.1.6.1 = 2544 | BC1 | 3 | 40 | 11 | 7 | 13 |
| pDAB105826.2.137.1::pDAB118233.1.6.1 = 2545 | BC1 | 5 | 40 | 11 | 8 | 11 |
| Summary Cross with Excisors | — | 106 | 800 | 168 | 109 | 218 |

| Event/Cross Name | # Excisor only - no target | # AAD1 Not Excised - Excisor present | # AAD1 Not Excised - No Excisor | Chi Square |
|---|---|---|---|---|
| pDAB118231{1}016.001 | — | — | 17 | 0.26 |
| pDAB118231{1}021.001 | — | — | 4 | 0.00 |
| pDAB118231{1}028.001 | — | — | 18 | 0.19 |
| pDAB118232{1}002.001 | — | — | 14 | 0.85 |
| pDAB118232{1}023.001 | — | — | 5 | 0.00 |
| pDAB118232{1}028.001 | — | — | 9 | 0.06 |
| pDAB118233{1}011.001 | — | — | 19 | 0.14 |
| pDAB118233{1}015.001 | — | — | 12 | 0.35 |
| pDAB118233{1}006.001 | — | — | 10 | 0.18 |
| Summary Controls | — | — | 108 | — |
| pDAB105826.2.137.1::pDAB118231.1.16.1 = 2528 | 11 | 0 | 0 | 0.10 |
| pDAB105826.2.137.1::pDAB118231.1.21.1 = 2521 | 7 | 0 | 0 | 0.40 |
| pDAB105826.2.137.1::pDAB118231.1.21.1 = 2522 | 10 | 0 | 0 | 0.52 |
| pDAB105826.2.137.1::pDAB118231.1.21.1 = 2523 | 9 | 0 | 0 | 0.50 |
| pDAB105826.2.137.1::pDAB118231.1.28.1 = 2529 | 2 | 0 | 0 | 0.34 |
| pDAB105826.2.137.1::pDAB118232.1.2.1 = 2524 | 18 | 0 | 0 | 0.87 |
| pDAB105826.2.137.1::pDAB118232.1.2.1 = 2525 | 9 | 0 | 0 | 0.00 |
| pDAB105826.2.137.1::pDAB118232.1.2.1 = 2526 | 10 | 0 | 0 | 0.05 |
| pDAB105826.2.137.1::pDAB118232.1.28.1 = 2534 | 8 | 4 | 15 | 0.00 |
| pDAB105826.2.137.1::pDAB118232.1.28.1 = 2535 | 4 | 10 | 13 | 0.00 |
| pDAB105826.2.137.1::pDAB118232.1.28.1 = 2536 | 0 | 0 | 17 | 0.00 |
| pDAB105826.2.137.1::pDAB118232.1.28.1 = 2537 | 4 | 0 | 0 | 0.04 |
| pDAB105826.2.137.1::pDAB118232.1.28.1 = 2538 | 5 | 0 | 0 | 0.26 |
| pDAB105826.2.137.1::pDAB118233.1.11.1 = 2539 | 4 | 0 | 0 | 0.25 |
| pDAB105826.2.137.1::pDAB118233.1.11.1 = 2540 | 4 | 0 | 0 | 0.68 |
| pDAB105826.2.137.1::pDAB118233.1.11.1 = 2541 | 7 | 0 | 0 | 0.27 |
| pDAB105826.2.137.1::pDAB118233.1.11.1 = 2542 | 1 | 0 | 0 | 0.00 |
| pDAB105826.2.137.1::pDAB118233.1.15.1 = 2543 | 16 | 0 | 0 | 0.63 |
| pDAB105826.2.137.1::pDAB118233.1.6.1 = 2544 | 6 | 0 | 0 | 0.62 |
| pDAB105826.2.137.1::pDAB118233.1.6.1 = 2545 | 5 | 0 | 0 | 0.61 |
| Summary Cross with Excisors | 140 | 14 | 45 | — |

TABLE 6

DNA sequencing interpretations

| Event cross name | Interpretation |
|---|---|
| B104[1]/pDAB105826.2.137.1::pDAB118231.1.21.1 = 2521 | Perfect |
| B104[1]/pDAB105826.2.137.1::pDAB118231.1.21.1 = 2522 | Perfect |
| B104[1]/pDAB105826.2.137.1::pDAB118231.1.21.1 =2523 | Perfect |
| B104[1]/pDAB105826.2.137.1::pDAB118231.1.28.1 = 2529 | Perfect |
| B104[1]/pDAB105826.2.137.1::pDAB118232.1.2.1 = 2524 | Perfect |
| B104[1]/pDAB105826.2.137.1::pDAB118232.1.2.1 = 2525 | Perfect |
| B104[1]/pDAB105826.2.137.1::pDAB118233.1.11.1 = 2539 | Perfect |
| B104[1]/pDAB105826.2.137.1::pDAB118233.1.11.1 = 2541 | Perfect |
| B104[1]/pDAB105826.2.137.1::pDAB118233.1.11.1 = 2542 | Perfect |
| B104[1]/pDAB105826.2.137.1::pDAB118232.1.2.1 = 2526 | Imperfect repair |
| B104[1]/pDAB105826.2.137.1::pDAB118232.1.28.1 = 2537 | Imperfect repair |

TABLE 6-continued

DNA sequencing interpretations

| Event cross name | Interpretation |
|---|---|
| B104[1]/pDAB105826.2.137.1::pDAB118232.1.28.1 = 2538 | Imperfect repair |
| B104[1]/pDAB105826.2.137.1::pDAB118233.1.6.1 = 2544 | Imperfect repair |
| B104[1]/pDAB105826.2.137.1::pDAB118233.1.6.1 = 2545 | Imperfect repair |
| B104[1]/pDAB105826.2.137.1::pDAB118233.1.11.1 = 2540 | No PCR product achieved |
| B104[1]/pDAB105826.2.137.1::pDAB118231.1.16.1 = 2528 | Bad sequence data |
| B104[1]/pDAB105826.2.137.1::pDAB118233.1.15.1 = 2543 | Perfect |

Example 10: Bioassay Results

The resulting transgenic events were advanced to bioassay to further characterize the inhibitory effect of the CRY proteins in insect bioassay. The transgenic events were assessed for root damage by western corn rootworm. Total protein of CRY34Ab1, CRY35Ab1, and AAD1 were isolated and quantified from the transgenic events. All of the transgenic events (e.g., pDAB118231, pDAB118232, and pDAB118233) showed inhibition of western corn rootworm activity as exemplified by calculating root damage scores (Table 7). In comparison, the control plants (e.g., B104) did not provide any inhibition of western corn rootworm activity (Table 7). Accordingly, the transgenic events containing a chloroplast transit peptide (TRAP 4, TRAP 8, or TRAP 12) linked to the cry34Ab1 transgene and stacked with the cry35Ab1 transgene robustly expressed the CRY34Ab1 and CRY35Ab1 proteins. Moreover, the transgenic events containing a chloroplast transit peptide (TRAP 4, TRAP 8, or TRAP 12) linked to the cry34Ab1 transgene and stacked with the cry35Ab1 transgene provided insect resistance to the transgenic plants.

TABLE 7

Summary of protein expression and root rating by construct

| Construct | AAD1 ng/cm2 | | Cry34Ab1 ng/cm2 | | Cry35Ab1 ng/cm2 | | Mean Root Rating |
|---|---|---|---|---|---|---|---|
| | Mean | Std Dev | Mean | Std Dev | Mean | Std Dev | |
| pDAB118231 | 49.54 | 13.19 | 148.65 | 115.30 | 164.62 | 37.73 | 0.02 |
| pDAB118232 | 42.77 | 22.40 | 425.86 | 261.99 | 149.00 | 35.23 | 0.01 |
| pDAB118233 | 39.73 | 11.08 | 261.15 | 47.59 | 173.98 | 26.22 | 0.01 |
| B104 | 0.13 | 0.35 | 0.00 | 0.00 | 0.00 | 0.00 | 1.00 |

Figure 7:
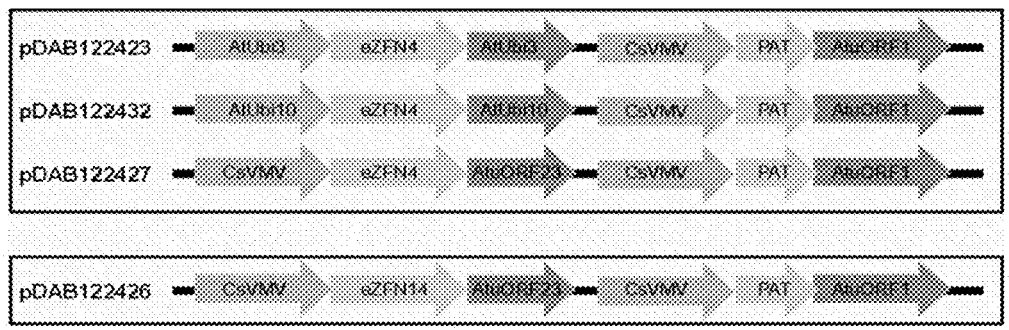
FIG. 7 is a schematic depicting the constructs used for transgenic soybean production.

Example 11: Design and Preparation of Excisor Constructs and Transgenic Soybean Production Leveraging the experience with zinc finger nuclease-mediated transgene deletion in tobacco and maize, and based on the cleavage results obtained by molecular methods in rapid testing assays, two eZFNs (eZFN4 and eZFN14) were identified for testing in soybean. Further, to identify suitable regulatory elements and the expression levels required for efficient excision, three different sets of regulatory elements, i.e., AtUbi10/AtUbi10, AtUbi3/AtUbi3, CsVMV/AtuORF23 (standard used in tobacco) were selected for testing in combination with eZFN4 (SEQ ID NO:22) and/or eZFN14 (SEQ ID NO:23). Four constructs (FIG. 7) were used for transgenic production to produce a total of 65 high quality events (Table 8).

11.1: Design and Construction of pDAB122423

The plasmid of pDAB122423 containing a first zinc finger nuclease gene expression cassette and a second pat gene expression cassette was designed and constructed using art recognized protocols. The resulting first zinc finger nuclease gene expression cassette contained the following gene elements; the *Arabidopsis thaliana* ubiquitin-3 promoter (AtUbi3; Callis et al. (1995) Genetics 139(2):921-39):: the coding sequence to the zinc finger nuclease gene that recognizes and cleaves eZFN4 (eZFN4; PCT/US2011/022145):: terminated by *Arabidopsis thaliana* ubiquitin-3. The second pat gene expression cassette contained the following elements; the cassava vein mosaic virus promoter (CsVMV; Verdaguer et al., 1996, Plant Molecular Biology 31:1129-1139):: the phosphinothricin acetyltransferase gene (pat; Wohlleben et al. (1988) Gene 70:25-37):: terminated by an *Agrobacterium tumifaciens* orf-1 3' UTR (AtuORF1; Huang et al., J. Bacteriol. 172:1814-1822). The assembly of this plasmid was confirmed via restriction enzyme digestion and sequencing reactions and is provided as FIG. 7.

11.2: Design and Construction of pDAB122432

Figure 8:
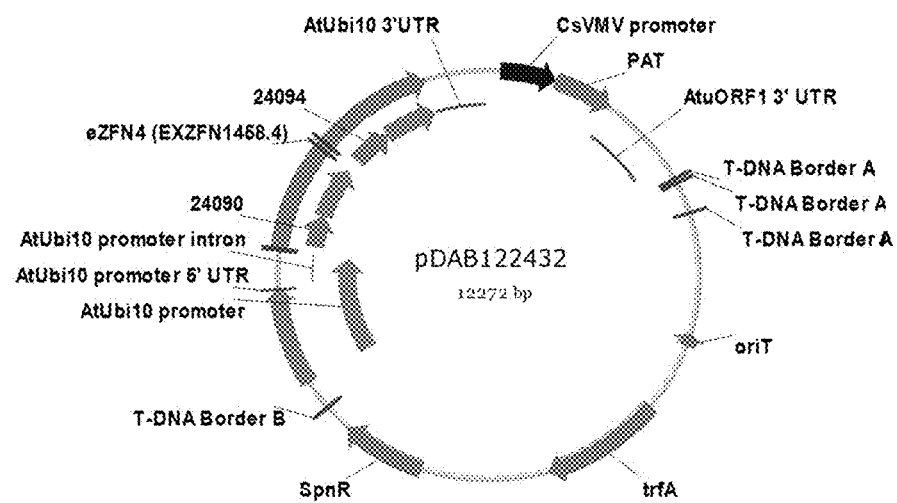
FIG. 8 is a schematic depicting a plasmid map of pDAB122432.
Figure 9:
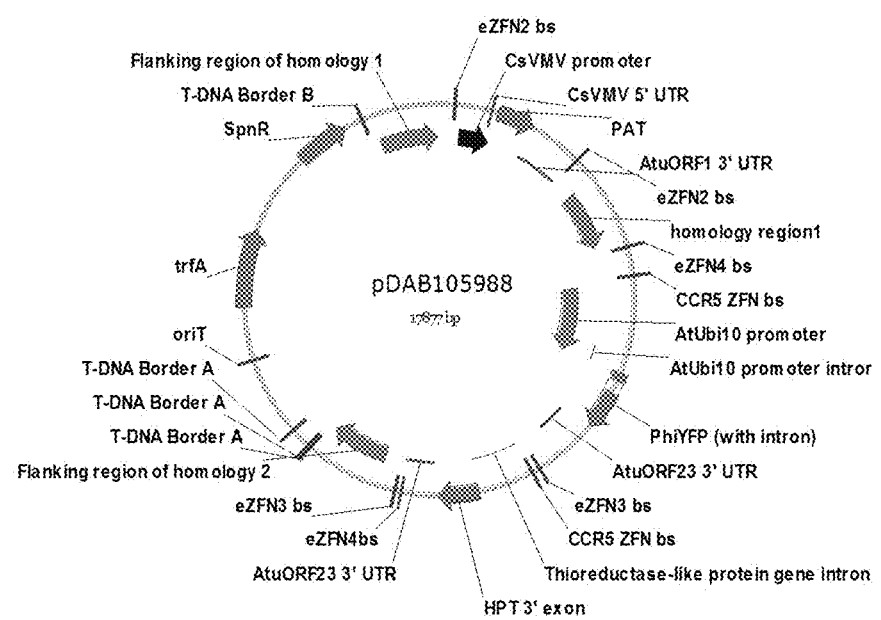
FIG. 9 is a schematic depicting a plasmid map of pDAB105984.

The plasmid of pDAB122432 containing a first zinc finger nuclease gene expression cassette and a second pat gene expression cassette was designed and constructed using art recognized protocols. The resulting first zinc finger nuclease gene expression cassette contained the following gene elements; the *Arabidopsis thaliana* ubiquitin-10 promoter (AtUbi10; Callis et al. (1990) J. Biol. Chem. 265:12486-93):: the coding sequence to the zinc finger nuclease gene that recognizes and cleaves eZFN4:: terminated by *Arabidopsis thaliana* ubiquitin-10. The second pat gene expression cassette contained the following elements; the CsVMV promoter:: the pat gene:: terminated by an AtuORF1. The assembly of this plasmid was confirmed via restriction enzyme digestion and sequencing reactions and is provided as FIGS. 7 and 8.

11.3: Design and Construction of pDAB122427

The plasmid of pDAB122427 containing a first zinc finger nuclease gene expression cassette and a second pat gene expression cassette was designed and constructed using art recognized protocols. The resulting first zinc finger nuclease gene expression cassette contained the following gene elements; the CsVMV promoter:: the coding sequence to the zinc finger nuclease gene that recognizes and cleaves eZFN4:: terminated by *Agrobacterium tumifaciens* orf-23 3' UTR (AtuORF23; Barker et al., Plant Molecular Biology 1983, 2(6), 335-50). The second pat gene expression cassette contained the following elements; the CsVMV promoter:: the pat gene:: terminated by an AtuORF1. The assembly of this plasmid was confirmed via restriction enzyme digestion and sequencing reactions and is provided as FIG. 7.

11.4: Design and Construction of pDAB122426

The plasmid of pDAB122426 containing a first zinc finger nuclease gene expression cassette and a second pat gene expression cassette was designed and constructed using art recognized protocols. The resulting first zinc finger nuclease gene expression cassette contained the following gene elements; the CsVMV promoter:: the coding sequence to the zinc finger nuclease gene that recognizes and cleaves eZFN14 (eZFN14; reference?):: terminated by *Agrobacterium tumifaciens* orf-23 3' UTR (AtuORF23; Barker et al., Plant Molecular Biology 1983, 2(6), 335-50). The second pat gene expression cassette contained the following elements; the CsVMV promoter:: the pat gene:: terminated by an AtuORF1. The assembly of this plasmid was confirmed via restriction enzyme digestion and sequencing reactions and is provided as FIG. 7.

11.5: Design and Construction of pDAB 105988

The plasmid of pDAB105988 containing a first pat gene expression cassette, a second yellow fluorescence (YFP) gene expression cassette and a partial hygromycin phosphotransferase gene cassette was designed and constructed using art recognized protocols. The resulting first pat gene expression cassette contained the following gene elements: the constitutive CsVMV gene promoter, the coding sequence to the pat, and the 3' untranslated region and terminator from the AtuORF23 gene. The second YFP gene cassette contained the following gene elements, an AtUbi10 promoter, the coding sequence to the *Phialidium* sp. yellow fluorescence protein (PhiYFP, Evrogen, Moscow, Russia), and the 3' untranslated region and terminator from the ORF1 gene of *Agrobacterium tumefaciens* (AtuORF1 3' UTR, (Barker et al., 1983)). The third partial HPT gene expression cassette contained the following gene elements: the *Arabidopsis thaliana* thioreductase-like protein gene intron (At3g25580), a 3' region of the hygromycin phosphotransferase gene (HPT (U.S. Pat. No. 5,668,298)), and the 3' untranslated region and terminator from the AtuORF23 gene. The pat gene cassette is flanked by binding sites for eZFN2 (PCT/US2011/022145); the pat YFP gene and HPT partial gene cassettes are flanked by binding sites for eZFN4 (PCT/US2011/022145), and the HPT partial gene is flanked cassette by eZFN3 (PCT/US2011/022145). In addition, there is a CCR5 ZFN binding site (U.S. Patent Publication No. 2008/0159996) between the YFP and partial HPT gene cassettes. An approximate 1 kb region of random DNA (U.S. Pat. No. 20150040267) is present between the pat and YFP gene cassettes. The assembly of this plasmid was confirmed via restriction enzyme digestion and sequencing reactions and is provided as FIG. 11.

Example 12: Plant Transformation and Molecular Confirmation of Transgenic Events The four constructs described above (FIG. 7) were introduced into the transformation line of *Glycine max* c.v. Maverick using *Agrobacterium*-based transformation. The method used for transgenic production is described in U.S. Patent Publication No. 2014/0173774 A1 and resulted in 65 high quality events (Table 8).

TABLE 8

Soybean transgenic production with four excisor constructs (abreviations BB = Back Bone, and GH = Greenhouse).

| Construct | Excisor construct description | Explants infected | Shoots regenerated | Shoots analyzed | 1-2 copy, BB free | Sent to GH | T1 seeds harvested |
|---|---|---|---|---|---|---|---|
| pDAB122423 | AtUbi3/eZFN4 | 808 | 121 | 121 | 65 | 14 | 11 |
| pDAB122426 | CsVMV/eZFN4 | 807 | 138 | 138 | 84 | 24 | 19 |
| pDAB122427 | CsVMV/eZFN14 | 806 | 147 | 147 | 94 | 28 | 21 |
| pDAB122432 | AtUbi10/eZFN4 | 807 | 135 | 135 | 72 | 17 | 14 |

For copy number analysis, leaf tissue was collected from fully expanded trifoliate leaves three weeks after seeding. Genomic DNA was extracted with a QIAGEN MagAttract™ kit (Valencia, Calif.) using THERMO FISHER KingFisher™ magnetic particle processors (Waltham, Mass.) and the supplier's recommended protocols. Transgene copy number analysis was performed using specific Hydrolysis Probe assays for the AAD12, PAT, YFP and ZFN genes. Hydrolysis Probe assays for endogenous soybean low copy conserved region GMS116 (GenBan™ Accession No. AK286292.1) were developed as internal reference standards.

Table 9 lists the oligonucleotide sequences of the Hydrolysis Probe assay components. Primers and BHQ probes were synthesized by INTEGRATED DNA TECHNOLOGIES (Coralville, Iowa), and MGB probes were synthesized by APPLIED BIOSYSTEMS (Grand Island, N.Y.). Biplex Hydrolysis Probe PCR reactions were set up according to Table 10 with about 10 ng of DNA, and assay conditions are presented in Table 11.

TABLE 9

List of forward and reverse nucleotide primer and fluorescent probes used for copy number analysis.

| Name | SEQ ID NO: | Oligo Sequence (5' → 3') |
|---|---|---|
| PAT_F | 11 | ACAAGAGTGGATTGATGATCTAGAGAGGT |
| PAT_P | 13 | 6FAM-GGTGTTGTGGCTGGTATTGCTTACGCTGG-BHQ |
| PAT_R | 12 | CTTTGATGCCTATGTGACACGTAAACAGT |
| AAD12_F | 24 | AACCCGTGCTCTTGTTC |
| AAD12_P | 25 | 6FAM-CAGGCCGGGTCAGCCT-BHQ |
| AAD12_R | 26 | GGATGCACCTTGACCAAT |

TABLE 9-continued

List of forward and reverse nucleotide primer and fluorescent probes used for copy number analysis.

| Name | SEQ ID NO: | Oligo Sequence (5' → 3') |
|---|---|---|
| YFP_F | 27 | CGTGTTGGGAAAGAACTTGGA |
| YFP_P | 28 | FAM-CACTCCCCACTGCCT-MGB |
| YFP_R | 29 | CCGTGGTTGGCTTGGTCT |
| FokI_F | 30 | TGAATGGTGGAAGGTGTATCC |
| FokI_P | 31 | FAM-CATCTGTTACAGAGTTCAAA-MGB |
| FokI_R | 32 | AAGCTGTGCTTTGTAGTTACCCTTA |
| GMS116_F | 33 | GTAATATGGGCTCAGAGGAATGGT |
| GMS116_P | 34 | Hex-CCATGGCCCGGTACCATCTGGTC-BHQ |
| GMS116_R | 35 | ATGGAGAAGAACATTGGAATTGC |

TABLE 10

PCR mixture for DNA copy number analysis.

| Number of Reactions | μl each | Final Concentration |
|---|---|---|
| H2O | 0.5 μL | |
| PVP (10%) | 0.1 μL | 0.10% |
| ROCHE 2X Master Mix | 5 μL | 1X |
| GOI Forward Primer (10 μM) | 0.4 μL | 0.4 μM |
| GOI Reverse Primer (10 μM) | 0.4 μL | 0.4 μM |
| GOI Probe (5 μM) | 0.4 μL | 0.2 μM |
| Reference Forward Primer (10 μM) | 0.4 μL | 0.4 μM |
| Reference Reverse Primer (10 μM) | 0.4 μL | 0.4 μM |
| Reference Probe (5 μM) | 0.4 μL | 0.2 μM |

TABLE 11

Thermocycler conditions for hydrolysis probe PCR amplification.

| PCR Steps | Temp (° C.) | Time | No. of cycles |
|---|---|---|---|
| Denature/Activation | 95 | 10 min | 1 |
| Denature | 95 | 10 sec | 40 |
| Anneal/Extend | 60 | 35 sec | |
| Acquire | 72 | 1 sec | |
| Cool | 40 | 10 sec | 1 |

For amplification, LIGHTCYCLER®480 Probes Master mix (Roche Applied Science, Indianapolis, Ind.) was prepared at 1× final concentration in a 10 μL volume multiplex reaction containing 0.1% of polyvinylpyrrolidine (PVP), 0.4 μM of each primer, and 0.2 μM of each probe. The FAM (6-Carboxy Fluorescein Amidite) fluorescent moiety was excited at 465 nm and fluorescence was measured at 510 nm; the corresponding values for the HEX (hexachlorofluorescein) fluorescent moiety were 533 nm and 580 nm, and for VIC® the values were 538 nm and 554 nm. The level of fluorescence generated for each reaction was analyzed using the Roche LightCycler®480 Real-Time PCR system according to the manufacturer's recommendations. Transgene copy number was determined by comparison of LightCycler®480 outputs of Target/Reference gene values for unknown samples to Target/Reference gene values of known copy number standards (1-Copy representing hemizygous plants, 2-Copy representing homozygous plants). Cp scores, i.e., the point at which the florescence signal crosses the background threshold using the fit points algorithm (LightCycler® software release 1.5), and the Relative Quant module (based on the ΔΔCt method), were used to perform the analysis of real time PCR data.

Out-out PCR was used to confirm the excision from target construct pDAB105988 with forward and reverse oligos flanking the two eZFN recognition sites. PCR amplification was performed with Biometra T Professional Thermacycler (Biometra GmbH, Goettingen, Germany) in 50 μl reactions containing 1.25 units of TaKaRa Ex Taq™ DNA polymerase (Takara Bio Inc., Shiga, Japan), 400 nM of dNTP, 200 nM each of forward (3176F: ATTGAGGGGATAAGGCCAAC; SEQ ID NO:36), reverse primers (9779R: TACTGCCGTGACGTAGCATC; SEQ ID NO:37) and 30 ng of genomic DNA. The following standard PCR program was used: 10 min of denaturing at 95° C.; 35 cycles of 98° C. for 15 seconds, 60° C. for 30 seconds and 72° C. for 45 seconds. Ten percent of the PCR products were visualized on a 2% agarose E-Gel (Life Technologies, Carlsbad, Calif.). The remaining reactions were purified using Purelink™ quick PCR purification kit and submitted to Eurofins MWG Operon (Huntsville, Ala.) for direct sequencing. DNA sequence analysis software Sequencher 4.10.1 (Gene Codes Corporation, Ann Arbor, Mich.) was used for alignment.

Example 13: Characterization and Selection of Excisor Lines and T2 Seed Production T1 events were characterized as per the criteria established for selection of Excisor lines, i.e., heritability, segregation, 1-2 copy, intact PTU, gene location and expression. Various activities including herbicide spray for heritability, DNA analysis for segregation and identification of homozygotes, copy number and absence of backbone, RNA analysis for expression, and NGS for intact PTU, were completed and a total of 8 Excisor lines (2 per construct—Table 12) were selected for crossing and grown in large pots to ensure sufficient T2 seed production from homozygous plants for making a large number of crosses.

TABLE 12

T1 events selected for T2 seed production and crossing based on copy number, absence of backbone, intact PTU, genomic location and RNA expression.

| ZFN | Construct | Sample | Copy # | Backbone | Intact PTU | Genomic Context | Genome Deletion (bp) | RNA (Homo mean) | RNA (Homo/Hemi) |
|---|---|---|---|---|---|---|---|---|---|
| ZFN14 | 122426 | 122426_3_079_001 | 1 | Clean | Yes | Intergenic | 18 | 11.9 | 0.8 |
| | | 122426_5_057_001 | 1 | Clean | Yes | Intergenic | 43 | 30.2 | 1.6 |
| ZFN4 | 122423 | 122423_2_040_001 | 1 | Clean | Yes | Intergenic | 5754 | 8.6 | 2 |
| | | 122423_3_084_001 | 1 | Clean | Yes | 5' UTR of Glyma06G114600 | 12 | 5.3 | 1.1 |

TABLE 12-continued

T1 events selected for T2 seed production and crossing based on copy number,
absence of backbone, intact PTU, genomic location and RNA expression.

| ZFN | Construct | Sample | Copy # | Backbone | Intact PTU | Genomic Context | Genome Deletion (bp) | RNA (Homo mean) | RNA (Homo/Hemi) |
|---|---|---|---|---|---|---|---|---|---|
| | 122427 | 122427_2_029_001 | 1 | Clean | Yes | NA | NA | 8.5 | 0.9 |
| | | 122427_2_099_001 | 1 | Clean | Yes | intron of Glyma14G091300 | 1 | 5.4 | 1.8 |
| | 122432 | 122432_1_004_001 | 1 | Clean | Yes | Intergenic | 40 | 7 | 1.5 |
| | | 122432_3_082_001 | 1 | Clean | 700 bp truncation at 5' | Intergenic | 12 | 3.5 | 1.6 |

Example 14: Crossing and Analysis of F1 Progeny

Figure 10:
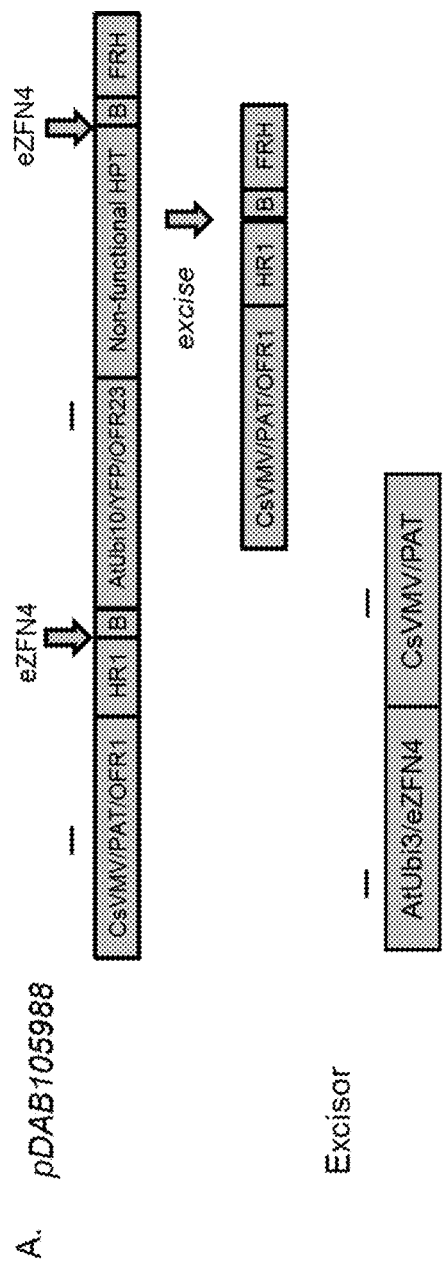
FIG. 10A and FIG. 10B is a schematic depicting a target construct, Excisor construct, and a hypothetical excised product for FIG. 10A. pDAB105988.
Figure 10:
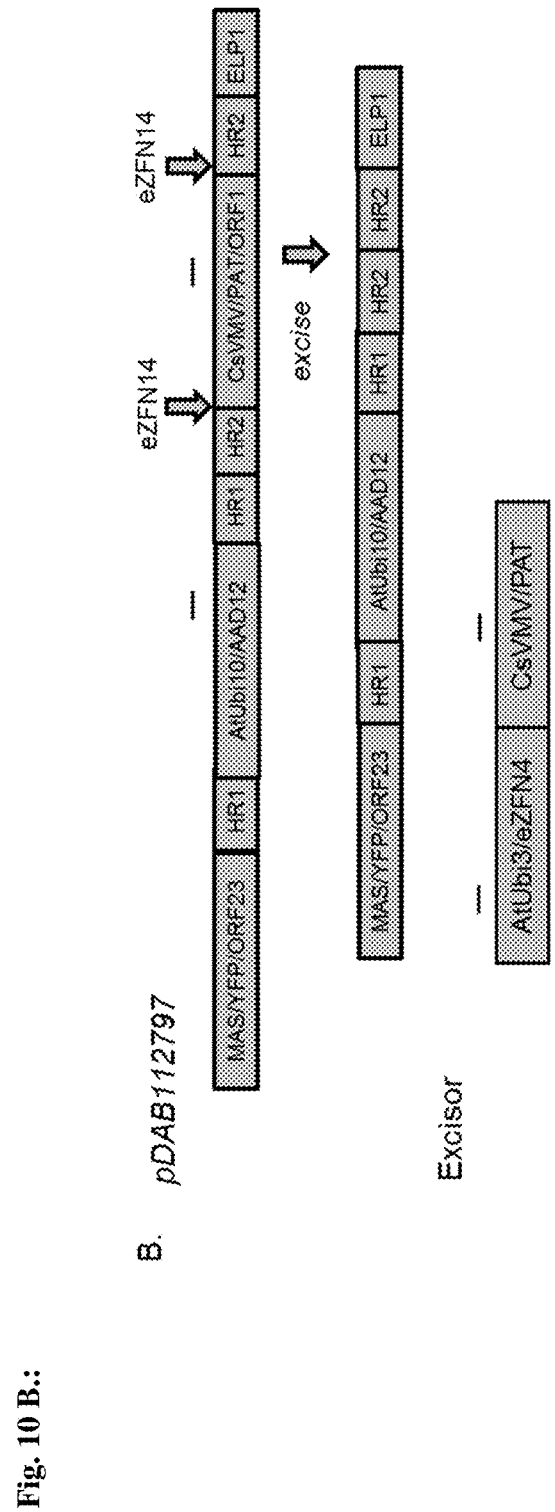
Figure 11:
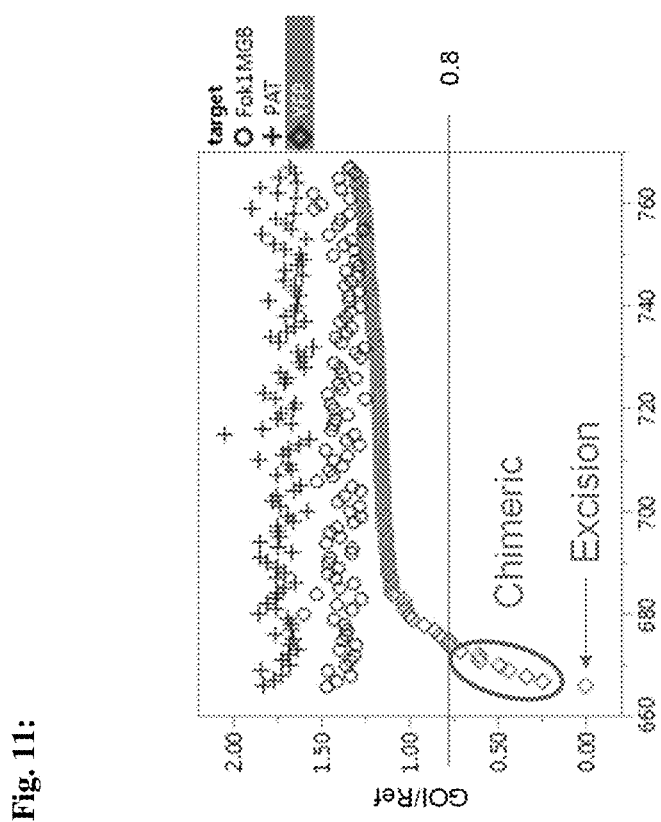
FIG. 11 is a graph depicting the results of three genes of interest: PAT, YFP and ZFN (measured using FokI probe/primers) for a subset of F1 plants from the cross: pDAB105988{19}104/pDAB105988.19.104.3.

A total of 6,480 crosses, involving 16 cross combinations (8 Excisor lines×2 reciprocal crosses), were completed. Of 3,818 F1 seed produced, 2,466 F1 progeny were analyzed by qPCR for PAT, YFP, AAD12 and ZFN in the F1 generation. F1 contains 1 copy of target and 1 copy of Excisor. For crosses with target line pDAB105988.19.104.003-1-6-99, F1 plants can be confirmed with 2 copies of PAT and 1 copy of the ZFN gene. Any plants with reduced YFP copy number (<1n) are potentially exhibiting excision (FIG. 10A). As indicated in FIG. 11, plants with YFP excised would have relatively no fluorescent signal generated from qPCR. These plants were classified as having complete excision. If the plants have intermediate signal (a relative ratio of YFP to endogenous reference GMS116 of 0.8 was used as the arbitrary cut off point), they were considered as chimeric excision. For crosses with target line pDAB112797.2.046.001-1-4, F1 plants that have not undergone excision could be confirmed as having 1 copy of AAD12, 2 copies of PAT and 1 copy of the ZFN gene. Any plant with a reduced PAT copy number (<2n) were potential candidates for excision (FIG. 10B).

Based on 2,466 F1 progeny analyzed with qPCR, plants with successful complete excision were identified from eZFN4 using 2 different promoter/terminator combinations, AtUbi10/eZFN4-HF/AtUbi10 and AtUbi3/eZFN4/AtUbi3, at frequencies of 1.23% and 0.13%, respectively (Table 13). Chimeric excision were detected in all four constructs, ranging from 1.58% to 10.68%.

TABLE 13

Excision frequencies detected with qPCR
in F1 population for eZFN4 and eZFN14.

| Constructs | Description | # of samples | % Complete Excision | % Chimeric Excision |
|---|---|---|---|---|
| pDAB122432 | AtUbi10/eZFN4-HF/AtUbi10 | 571 | 1.23% | 10.68% |
| pDAB122423 | AtUbi3/eZFN4/AtUbi3 | 767 | 0.13% | 4.43% |
| pDAB122427 | CsVMV/eZFN4/AtuORF23 | 505 | 0.00% | 1.58% |
| pDAB122426 | CsVMV/eZFN14/AtuORF23 | 319 | 0.00% | 2.82% |

Example 15: Analysis in F2 Generation

To test if the YFP excision was transmitted to the next generation, F2 progeny of 18 F1 plants were grown in the greenhouse and subjected to copy number analysis with qPCR on PAT, YFP and ZFN4. (The F1 parents were derived from a cross of Excisor ZFN4 pDAB122432.3.082 with Target line pDAB105988.19.104; 1 exhibited complete excision, 6 were chimeric and 11 showed no evidence of excision.) Any F2 plants identified as lacking YFP by qPCR, were further confirmed to have undergone excision using out-out PCR. Excision footprints were then revealed with amplicon sequencing.

To calculate the excision rate, plants that did not inherit any target locus (nulls and Excisor-only plants) were excluded from summary (Table 14). In the case of one event that showed complete excision in the F1 generation, all F2 plants with target had excised YFP as expected, confirming 100% heritability. For plants with no excision detected in the F1 generation, there was still a 0.63% complete excision in the F2. Chimeric F1 events had 2.06% complete excision in the F2 generation.

TABLE 14

Excision frquencies detected with qPCR in
F2 populations based on F1 genotypes.

| | F2 Analysis | | |
|---|---|---|---|
| F1 Analysis | # Plants with Target Event | # Plants Excised | % Complete Excision |
| Excision | 14 | 14 | 100 |
| Non-Excised | 478 | 3 | 0.63 |
| Chimeric | 194 | 5 | 2.58 |

Complete excised F2 plants were confirmed with out-out PCR using forward and reverse oligos flanking the two eZFN4 recognition sites on pDAB105988. The PCR product were then sent for amplicon Sanger sequencing. The sequencing results indicated that the ZFN binding sites were restored after the complete excision of YFP for the plants no longer containing Excisor elements. For excised F2 plants with copies of Excisor, the newly repaired ZFN binding sites were being subjected to continuous creation of DSBs and imperfect repairs, leading to chimeric footprint with indels.

While aspects of this invention have been described in certain embodiments, they can be further modified within the spirit and scope of this disclosure. This application is therefore intended to cover any variations, uses, or adaptations of embodiments of the invention using its general principles. Further, this application is intended to cover such departures from the present disclosure as come within known or customary practice in the art to which these embodiments pertains and which fall within the limits of the appended claim.

What may be claimed is:

1. A method for producing a repaired site specific nuclease binding site within a plant, the method comprising the following steps:
   a. Providing a plant genome comprising a first copy of a site specific nuclease binding site, an intervening polynucleotide sequence, and a second copy of the site specific nuclease binding site, wherein the first copy of the site specific nuclease binding site and the second copy of the site specific nuclease binding site are identical, and the first copy of the site specific nuclease binding site is located within 3,000 bp to 4,000 bp of the second copy of the site specific nuclease binding site;
   b. Introducing a site specific nuclease designed to bind and cleave at the site specific nuclease binding site;
   c. Cleaving the first copy of the site specific nuclease binding site;
   d. Cleaving the second copy of the site specific nuclease binding site;
   e. Excising the intervening polynucleotide sequence from the plant genome;
   f. Recombining the first cleaved site specific nuclease binding site with the second cleaved site specific nuclease binding site;
   g. Producing the repaired site specific nuclease binding site, wherein the repaired site specific nuclease binding site is repaired via a NHEJ-mediated cellular process and the repaired site specific nuclease binding site is identical to the first copy of the site specific nuclease binding site.

2. The method of claim 1, wherein the site specific nuclease is selected from the group consisting of a Zinc Finger nuclease, a CRISPR nuclease, a TALEN nuclease, or any combination thereof.

3. The method of claim 2, wherein the Zinc Finger nuclease comprise a FokI nuclease.

4. The method of claim 3, wherein the FokI nuclease comprises a high fidelity FokI nuclease.

5. The method of claim 1, wherein the intervening polynucleotide sequence is completely removed from the plant genome.

6. The method of claim 5, wherein the intervening polynucleotide sequence comprises a transgene.

7. The method of claim 6, wherein the transgene encodes a selectable marker.

8. The method of claim 1, wherein the repaired site specific nuclease binding site is greater than 6 bp in length.

9. The method of claim 1, wherein the repaired site specific nuclease does not comprise an INDEL.

10. The method of claim 1, wherein the first copy of the site specific nuclease binding site, the intervening polynucleotide sequence, and the second copy of the site specific nuclease comprise either a native plant genomic sequence or a transgenic sequence within a plant genome.

11. The method of claim 1, the method further comprising the steps of:
   h. Targeting the repaired site specific nuclease binding site with the site specific nuclease;
   i. Cleaving the repaired site specific nuclease binding site with the site specific nuclease;
   j. Introducing a donor polynucleotide sequence;
   k. Integrating the donor polynucleotide sequence within the cleaved site specific nuclease binding site; and
   l. Producing a plant genome comprising the donor polynucleotide sequence stably integrated within the plant genome.

12. The method of claim 1, wherein the intervening polynucleotide sequence comprises a polynucleotide encoding a transgene or a gene expression cassette.

13. The method of claim 1, wherein the site specific nuclease binding site is palindromic.

14. The method of claim 1, wherein the site specific nuclease binding site is non-palindromic.

15. The method of claim 1, wherein the repaired site specific nuclease binding site is inherited in a progeny.

* * * * *

SEQUENCE LISTING

<160> NUMBER OF SEQ ID NOS: 37

<210> SEQ ID NO 1
<211> LENGTH: 37
<212> TYPE: DNA
<213> ORGANISM: Artificial
<220> FEATURE:
<223> OTHER INFORMATION: Unique binding site for site specific nuclease

<400> SEQUENCE: 1
aagactcccg cccatctctc tatgcccggg acaagtg                              37

<210> SEQ ID NO 2
<211> LENGTH: 22
<212> TYPE: DNA
<213> ORGANISM: Artificial
<220> FEATURE:
<223> OTHER INFORMATION: Primer sequence

<400> SEQUENCE: 2
tgacacaaag ctgaaagact at                                              22

<210> SEQ ID NO 3
<211> LENGTH: 22
<212> TYPE: DNA
<213> ORGANISM: Artificial
<220> FEATURE:
<223> OTHER INFORMATION: Primer sequence

<400> SEQUENCE: 3
ttgaggatgt agtaaggagt gg                                              22

<210> SEQ ID NO 4
<211> LENGTH: 17
<212> TYPE: DNA
<213> ORGANISM: Artificial
<220> FEATURE:
<223> OTHER INFORMATION: Primer/probe sequence

<400> SEQUENCE: 4
acgctggtgc cgtgtat                                                    17

<210> SEQ ID NO 5
<211> LENGTH: 20
<212> TYPE: DNA
<213> ORGANISM: Artificial
<220> FEATURE:
<223> OTHER INFORMATION: primer sequence

<400> SEQUENCE: 5
tgttcggttc cctctaccaa                                                 20

<210> SEQ ID NO 6
<211> LENGTH: 22
<212> TYPE: DNA
<213> ORGANISM: Artificial
<220> FEATURE:
<223> OTHER INFORMATION: Primer sequence

<400> SEQUENCE: 6
caacatccat caccttgact ga                                              22

<210> SEQ ID NO 7
<211> LENGTH: 24
<212> TYPE: DNA
<213> ORGANISM: Artificial

```
<220> FEATURE:
<223> OTHER INFORMATION: primer/probe sequence

<400> SEQUENCE: 7
cacagaaccg tcgcttcagc aaca                                          24

<210> SEQ ID NO 8
<211> LENGTH: 22
<212> TYPE: DNA
<213> ORGANISM: Artificial
<220> FEATURE:
<223> OTHER INFORMATION: Primer sequence

<400> SEQUENCE: 8
tggttatgac aggctccgtt ta                                            22

<210> SEQ ID NO 9
<211> LENGTH: 23
<212> TYPE: DNA
<213> ORGANISM: Artificial
<220> FEATURE:
<223> OTHER INFORMATION: Primer sequence

<400> SEQUENCE: 9
aacaaacctc ctggctactt caa                                           23

<210> SEQ ID NO 10
<211> LENGTH: 17
<212> TYPE: DNA
<213> ORGANISM: Artificial
<220> FEATURE:
<223> OTHER INFORMATION: Primer/probe sequence

<400> SEQUENCE: 10
cttgctggtg ttatgtg                                                  17

<210> SEQ ID NO 11
<211> LENGTH: 29
<212> TYPE: DNA
<213> ORGANISM: Artificial
<220> FEATURE:
<223> OTHER INFORMATION: Primer sequence

<400> SEQUENCE: 11
acaagagtgg attgatgatc tagagaggt                                     29

<210> SEQ ID NO 12
<211> LENGTH: 29
<212> TYPE: DNA
<213> ORGANISM: Artificial
<220> FEATURE:
<223> OTHER INFORMATION: Primer sequence

<400> SEQUENCE: 12
ctttgatgcc tatgtgacac gtaaacagt                                     29

<210> SEQ ID NO 13
<211> LENGTH: 29
<212> TYPE: DNA
<213> ORGANISM: Artificial
<220> FEATURE:
<223> OTHER INFORMATION: Primer/probe sequence

<400> SEQUENCE: 13
ggtgttgtgg ctggtattgc ttacgctgg                                     29
```

```
<210> SEQ ID NO 14
<211> LENGTH: 18
<212> TYPE: DNA
<213> ORGANISM: Artificial
<220> FEATURE:
<223> OTHER INFORMATION: Primer sequence

<400> SEQUENCE: 14
tggcggacga cgacttgt                                                     18

<210> SEQ ID NO 15
<211> LENGTH: 19
<212> TYPE: DNA
<213> ORGANISM: Artificial
<220> FEATURE:
<223> OTHER INFORMATION: Primer sequence

<400> SEQUENCE: 15
aaagtttgga ggctgccgt                                                    19

<210> SEQ ID NO 16
<211> LENGTH: 21
<212> TYPE: DNA
<213> ORGANISM: Artificial
<220> FEATURE:
<223> OTHER INFORMATION: Primer/probe sequence

<400> SEQUENCE: 16
cgagcagacc gccgtgtact t                                                 21

<210> SEQ ID NO 17
<211> LENGTH: 74
<212> TYPE: DNA
<213> ORGANISM: Artificial
<220> FEATURE:
<223> OTHER INFORMATION: Sequencing results of the repaired binding site
      that was cut by a site specific nuclease and recombined to produce
      a binding site that can be recleaved by the same site specific
      nuclease
<220> FEATURE:
<221> NAME/KEY: eZFN2 Binding Site
<222> LOCATION: (21)..(57)

<400> SEQUENCE: 17
tggatcgttc tttcatgtag aagactcccg cccatctctc tatgcccggg acaagtggta      60
catgataacc tcag                                                        74

<210> SEQ ID NO 18
<211> LENGTH: 3453
<212> TYPE: DNA
<213> ORGANISM: artificial sequence
<220> FEATURE:
<223> OTHER INFORMATION: The AAD-1 Gene expression Cassette that was
      flanked by the eZFN2 Binding Sites
<220> FEATURE:
<221> NAME/KEY: eZFN2 binding site
<222> LOCATION: (1)..(37)
<220> FEATURE:
<221> NAME/KEY: eZFN2 binding site
<222> LOCATION: (3417)..(3453)

<400> SEQUENCE: 18
aagactcccg cccatctctc tatgcccggg acaagtgggc gcgccaagct tgcatgcctg      60
cagatccccg gggatctccg cggagtgtgc agcgtgaccc ggtcgtgccc ctctctagag     120
ataatgagca ttgcatgtct aagttataaa aaattaccac atattttttt tgtcacactt     180
```

```
gtttgaagtg cagtttatct atctttatac atatatttaa acttactct acgaataata      240 taatctatag tactacaata atatcagtgt tttagagaat catataaatg aacagttaga      300
catggtctaa aggacaattg agtattttga caacaggact ctacagtttt atcttttag       360 tgtgcatgtg ttctcctttt tttttgcaaa tagcttcacc tatataatac ttcatccatt      420
ttattagtac atccatttag ggtttagggt taatggtttt tatagactaa ttttttagt       480 acatctattt tattctattt tagcctctaa attaagaaaa ctaaaactct attttagttt      540
ttttatttaa tagtttagat ataaaataga ataaaataaa gtgactaaaa attaaacaaa      600
taccctttaa gaaattaaaa aaactaagga aacattttc ttgtttcgag tagataatgc       660
cagcctgtta aacgccgtcg acgagtctaa cggacaccaa ccagcgaacc agcagcgtcg      720
cgtcgggcca agcgaagcag acggcacggc atctctgtcg ctgcctctgg accctctcg      780 agagttccgc tccaccgttg gacttgctcc gctgtcggca tccagaaatt gcgtggcgga      840
gcggcagacg tgagccggca cggcaggcgg cctcctcctc ctctcacggc accggcagct      900
acgggggatt cctttcccac cgctccttcg ctttcccttc ctcgcccgcc gtaataaata     960
gacaccccct ccacccctc ttccccaac ctcgtgttgt tcggagcgca cacacacaca      1020
accagatctc ccccaaatcc acccgtcggc acctccgctt caaggtacgc cgctcgtcct     1080 ccccccccc cccctctct accttctcta gatcggcgtt ccggtccatg catggttagg       1140
gcccggtagt tctacttctg ttcatgtttg tgttagatcc gtgtttgtgt tagatccgtg     1200
ctgctagcgt tcgtacacgg atgcgacctg tacgtcagac acgttctgat tgctaacttg     1260
ccagtgtttc tctttgggga atcctgggat ggctctagcc gttccgcaga cgggatcgat     1320
ttcatgattt ttttgtttc gttgcatagg gtttggtttg ccttttcct ttatttcaat       1380 atatgccgtg cacttgtttg tcgggtcatc ttttcatgct ttttttgtc ttggttgtga      1440 tgatgtggtc tggttgggcg gtcgttctag atcggagtag aattctgttt caaactacct     1500
ggtggattta ttaattttgg atctgtatgt gtgtgccata catattcata gttacgaatt     1560
gaagatgatg gatggaaata tcgatctagg ataggtatac atgttgatgc gggttttact    1620
gatgcatata cagagatgct ttttgttcgc ttggttgtga tgatgtggtg tggttgggcg    1680
gtcgttcatt cgttctagat cggagtagaa tactgtttca aactacctgg tgtatttatt    1740 aatttggaa ctgtatgtgt gtgtcataca tcttcatagt tacgagttta agatggatgg     1800
aaatatcgat ctaggatagg tatacatgtt gatgtgggtt ttactgatgc atatacatga    1860
tggcatatgc agcatctatt catatgctct aaccttgagt acctatctat tataataaac    1920
aagtatgttt tataattatt tcgatcttga tacttggga tgatggcata tgcagcagct     1980
atatgtggat ttttttagcc ctgccttcat acgctattta tttgcttggt actgtttctt    2040
ttgtcgatgc tcaccctgtt gtttggtgtt acttctgcag gtacagtagt tagttgaggt    2100
accggatcca cacgacacca tggctcatgc tgccctcagc cctctctccc aacgctttga    2160
gagaatagct gtccagccac tcactggtgt ccttggtgct gagatcactg gagtggactt    2220
gagggaacca cttgatgaca gcacctggaa tgagatattg gatgccttcc acacttacca    2280
agtcatctac ttcctggcc aagcaatcac caatgagcag cacattgcat tctcaagaag    2340
gtttggacca gttgatccag tgcctcttct caagagcatt gaaggctatc cagaggttca   2400
gatgatccgc agagaagcca atgagtctgg aagggtgatt ggtgatgact ggcacacaga   2460
ctccactttc cttgatgcac ctccagctgc tgttgtgatg agggcataga tgttcctga    2520 gcatggcgga gacactgggt tcctttcaat gtacacagct tgggagacct tgtctccaac    2580
```

```
catgcaagcc accatcgaag ggctcaacgt tgtgcactct gccacacgtg tgttcggttc    2640
cctctaccaa gcacagaacc gtcgcttcag caacaccctca gtcaaggtga tggatgttga    2700
tgctggtgac agagagacag tccatcccctt ggttgtgact catcctggct ctggaaggaa    2760
aggcctttat gtgaatcaag tctactgtca gagaattgag gcatgacag atgcagaatc    2820 aaagccattg cttcagttcc tctatgagca tgccaccaga tttgacttca cttgccgtgt    2880
gaggtggaag aaagaccaag tccttgtctg gacaacttg tgcaccatgc accgtgctgt    2940
tcctgactat gctggcaagt tcagatactt gactcgcacc acagttggtg gagttaggcc    3000
tgcccgctga gtagttagct taatcaccta gagctcggtc gcagcgtgtg cgtgtccgtc    3060
gtacgttctg gccggccggg ccttgggcgc gcgatcagaa gcgttgcgtt ggcgtgtgtg    3120
tgcttctggt ttgctttaat tttaccaagt ttgtttcaag gtggatcgcg tggtcaaggc    3180
ccgtgtgctt taaagaccca ccggcactgg cagtgagtgt tgctgcttgt gtaggctttg    3240
gtacgtatgg gctttatttg cttctggatg ttgtgtacta cttgggtttg ttgaattatt    3300
atgagcagtt gcgtattgta attcagctgg gctacctgga cattgttatg tattaataaa    3360
tgctttgctt tcttctaaag atctttaagt gctgaattca tatttcctcc tgcaggaaga    3420
ctcccgccca tctctctatg cccgggacaa gtg                                  3453
```

<210> SEQ ID NO 19
<211> LENGTH: 585
<212> TYPE: DNA
<213> ORGANISM: Artificial sequence
<220> FEATURE:
<223> OTHER INFORMATION: TRAP4 and Cry34ab1 fusion gene

<400> SEQUENCE: 19

```
tcaggattta tggccgtagc ggctggaggt ggtctggata gtataggtca cgtgggattg     60
attgccgctg ccaccttggg tgatgatttc atactgggat ttattggagt ggccgtcgta    120
tttattgctg ccagcgaacg ggttgtcgaa gtacaggctg atctccgcct cgccgttgat    180
ggagtagtag atggtgccct cggtgccggt catgaagccg tttgattcgg ccacgaaggt    240
tttaatttgg tcgttcgcca cgttggtcgg gctggtcctc cagcggccac cgtcaagttt    300
cgttttatcc tccagctgca atgtatggcc agtcttatta ttcacgtcga tgtgcacctc    360
cctcgcggac atggagcaga cggttgtctg aagtctgcga gtcgagcgga tggatgactt    420
ggagcacgac ctcctcgcga cgctcagagg agccgaatag acatgggaa ccacgtcgtt    480 gacgcttatg ggtctcggaa caaccaacgc tcccacctcc acgcgtctcg cgaggccagc    540
gttacactga gaggctctca gtgatcctcc ttggcgagcc aacat                     585
```

<210> SEQ ID NO 20
<211> LENGTH: 570
<212> TYPE: DNA
<213> ORGANISM: Artificial sequence
<220> FEATURE:
<223> OTHER INFORMATION: Trap8 and Cry34Ab1 fusion gene

<400> SEQUENCE: 20

```
atggctcaat ctagcagaat ctgccacggt gtgcagaacc catgtgtgat catttccaat     60
ctctccaaat ccaaccagaa caaatctcct ttctcagtca gcctcaagac tcaccagcag    120
cagcgtcgtg cttaccagat atctagctgg ggattgaaga agtcaaacaa cgggtccgtg    180
attcgtccgg ttaaggcaat gtccgcgagg gaggtgcaca tcgacgtgaa taataagact    240
```

```
ggccatacat tgcagctgga ggataaaacg aaacttgacg gtggccgctg gaggaccagc    300
ccgaccaacg tggcgaacga ccaaattaaa accttcgtgg ccgaatcaaa cggcttcatg    360
accggcaccg agggcaccat ctactactcc atcaacggcg aggcggagat cagcctgtac    420
ttcgacaacc cgttcgctgg cagcaataaa tacgacggcc actccaataa atcccagtat    480
gaaatcatca cccaaggtgg cagcggcaat caatcccacg tgacctatac tatccagacc    540
acctccagcc gctacggcca taaatcctga                                     570

<210> SEQ ID NO 21
<211> LENGTH: 594
<212> TYPE: DNA
<213> ORGANISM: Artificial sequence
<220> FEATURE:
<223> OTHER INFORMATION: TRAP12 and cry34ab1 fusion gene

<400> SEQUENCE: 21
atggcgcagt cctctaggat ctgccacggc gtgcagaacc cgtgcgtgat catctcgaac     60
ctgtccaagt ccaaccagaa caagtccccg ttctccgtga gcctcaagac ccaccagcac    120
ccgagggcct acccgatcag cagctcctgg ggcctgaaga gagcggcat gaccctgatc     180 ggctccgagc tgaggccgct gaaggtgatg tcaagcgtga gcatgtccgc gagggaggtg    240
cacatcgacg tgaataataa gactggccat acattgcagc tggaggataa aacgaaactt    300
gacggtggcc gctggaggac cagcccgacc aacgtggcga cgaccaaat taaaaccttc    360 gtggccgaat caaacggctt catgaccggc accgagggca ccatctacta ctccatcaac    420
ggcgaggcgg agatcagcct gtacttcgac aacccgttcg ctggcagcaa taaatacgac    480
ggccactcca ataaatccca gtatgaaatc atcacccaag gtggcagcgg caatcaatcc    540
cacgtgacct atactatcca gaccacctcc agccgctacg gccataaatc ctga          594

<210> SEQ ID NO 22
<211> LENGTH: 36
<212> TYPE: DNA
<213> ORGANISM: Artificial Sequence
<220> FEATURE:
<223> OTHER INFORMATION: eZFN4 binding site

<400> SEQUENCE: 22 gcctttgca gtttatctct atgcccggga caagtg                                36

<210> SEQ ID NO 23
<211> LENGTH: 36
<212> TYPE: DNA
<213> ORGANISM: Artificial Sequence
<220> FEATURE:
<223> OTHER INFORMATION: eZFN14 binding site

<400> SEQUENCE: 23
tggtcatcct catcctgtct atgcccggga caagtg                               36

<210> SEQ ID NO 24
<211> LENGTH: 17
<212> TYPE: DNA
<213> ORGANISM: Artificial Sequence
<220> FEATURE:
<223> OTHER INFORMATION: forward primer for AAD-12

<400> SEQUENCE: 24
aacccgtgct cttgttc                                                    17
```

```
<210> SEQ ID NO 25
<211> LENGTH: 16
<212> TYPE: DNA
<213> ORGANISM: Artificial Sequence
<220> FEATURE:
<223> OTHER INFORMATION: probe for AAD-12

<400> SEQUENCE: 25
caggccgggt cagcct                                                         16

<210> SEQ ID NO 26
<211> LENGTH: 18
<212> TYPE: DNA
<213> ORGANISM: Artificial Sequence
<220> FEATURE:
<223> OTHER INFORMATION: reverse primer for AAD-12

<400> SEQUENCE: 26
ggatgcacct tgaccaat                                                       18

<210> SEQ ID NO 27
<211> LENGTH: 21
<212> TYPE: DNA
<213> ORGANISM: Artificial Sequence
<220> FEATURE:
<223> OTHER INFORMATION: forward primer for YFP

<400> SEQUENCE: 27
cgtgttggga agaacttgg a                                                    21

<210> SEQ ID NO 28
<211> LENGTH: 15
<212> TYPE: DNA
<213> ORGANISM: Artificial Sequence
<220> FEATURE:
<223> OTHER INFORMATION: probe for YFP

<400> SEQUENCE: 28
cactccccac tgcct                                                          15

<210> SEQ ID NO 29
<211> LENGTH: 18
<212> TYPE: DNA
<213> ORGANISM: Artificial Sequence
<220> FEATURE:
<223> OTHER INFORMATION: reverse primer for YFP

<400> SEQUENCE: 29
ccgtggttgg cttggtct                                                       18

<210> SEQ ID NO 30
<211> LENGTH: 21
<212> TYPE: DNA
<213> ORGANISM: Artificial Sequence
<220> FEATURE:
<223> OTHER INFORMATION: forward primer for FokI

<400> SEQUENCE: 30
tgaatggtgg aaggtgtatc c                                                   21

<210> SEQ ID NO 31
<211> LENGTH: 20
<212> TYPE: DNA
<213> ORGANISM: Artificial Sequence
<220> FEATURE:
<223> OTHER INFORMATION: probe for FokI
```

```
<400> SEQUENCE: 31
catctgttac agagttcaaa                                                  20

<210> SEQ ID NO 32
<211> LENGTH: 25
<212> TYPE: DNA
<213> ORGANISM: Artificial Sequence
<220> FEATURE:
<223> OTHER INFORMATION: reverse primer for FokI

<400> SEQUENCE: 32
aagctgtgct ttgtagttac cctta                                            25

<210> SEQ ID NO 33
<211> LENGTH: 24
<212> TYPE: DNA
<213> ORGANISM: Artificial Sequence
<220> FEATURE:
<223> OTHER INFORMATION: forward primer for GMS116

<400> SEQUENCE: 33
gtaatatggg ctcagaggaa tggt                                             24

<210> SEQ ID NO 34
<211> LENGTH: 23
<212> TYPE: DNA
<213> ORGANISM: Artificial Sequence
<220> FEATURE:
<223> OTHER INFORMATION: probe for GMS116

<400> SEQUENCE: 34
ccatggcccg gtaccatctg gtc                                              23

<210> SEQ ID NO 35
<211> LENGTH: 23
<212> TYPE: DNA
<213> ORGANISM: Artificial Sequence
<220> FEATURE:
<223> OTHER INFORMATION: reverse primer for GMS116

<400> SEQUENCE: 35
atggagaaga acattggaat tgc                                              23

<210> SEQ ID NO 36
<211> LENGTH: 20
<212> TYPE: DNA
<213> ORGANISM: Artificial Sequence
<220> FEATURE:
<223> OTHER INFORMATION: 3176F forward primer for out-out PCR

<400> SEQUENCE: 36
attgagggga taaggccaac                                                  20

<210> SEQ ID NO 37
<211> LENGTH: 20
<212> TYPE: DNA
<213> ORGANISM: Artificial Sequence
<220> FEATURE:
<223> OTHER INFORMATION: 9779R reverse primer for out-out PCR

<400> SEQUENCE: 37
tactgccgtg acgtagcatc                                                  20
```